United States Patent
Cassell et al.

(10) Patent No.: US 11,173,003 B2
(45) Date of Patent: Nov. 16, 2021

(54) SYSTEMS AND METHODS FOR USING A ROBOTIC MEDICAL SYSTEM

(71) Applicant: INTUITIVE SURGICAL OPERATIONS, INC., Sunnyvale, CA (US)

(72) Inventors: Scott L. Cassell, Santa Clara, CA (US); David W. Bailey, Portola Valley, CA (US); Stephen J. Blumenkranz, Los Altos, CA (US); Timothy D. Boucher, Sunnyvale, CA (US); Matthew D. Rohr Daniel, San Francisco, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 187 days.

(21) Appl. No.: 16/471,737

(22) PCT Filed: Jan. 9, 2018

(86) PCT No.: PCT/US2018/012995
§ 371 (c)(1),
(2) Date: Jun. 20, 2019

(87) PCT Pub. No.: WO2018/132386
PCT Pub. Date: Jul. 19, 2018

(65) Prior Publication Data
US 2020/0022762 A1 Jan. 23, 2020

Related U.S. Application Data

(60) Provisional application No. 62/444,804, filed on Jan. 10, 2017.

(51) Int. Cl.
*A61B 34/00* (2016.01)
*A61B 34/30* (2016.01)
(Continued)

(52) U.S. Cl.
CPC .............. *A61B 34/30* (2016.02); *A61B 34/71* (2016.02); *A61B 34/37* (2016.02); *A61B 2034/301* (2016.02); *A61B 2090/504* (2016.02)

(58) Field of Classification Search
CPC ... A61B 34/30; A61B 34/71; A61B 2090/504; A61B 2034/301; A61B 34/37;
(Continued)

(56) References Cited

U.S. PATENT DOCUMENTS

| 5,807,377 A | 9/1998 | Madhani et al. |
| 8,220,765 B2 * | 7/2012 | Bailey ..................... F16F 15/28 248/325 |

(Continued)

FOREIGN PATENT DOCUMENTS

| CN | 104887288 A | 9/2015 |
| WO | WO-2005089113 A2 | 9/2005 |

(Continued)

OTHER PUBLICATIONS

"Carlos Gonzalez, "What's the Difference Between Spur, Helical, Bevel, and Worm Gears?", Jul. 30, 2015, MachineDesign" (Year: 2015).*

(Continued)

*Primary Examiner* — Joseph M Dietrich
*Assistant Examiner* — Michael T. Holtzclaw
(74) *Attorney, Agent, or Firm* — Haynes and Boone, LLP

(57) ABSTRACT

A medical system including a support structure including a proximal link and a distal link, and a base joint coupling the proximal link of the support structure to a base, wherein the proximal link is configured to rotate about a first axis associated with the base joint. The system also includes a linkage mechanism coupling the proximal link to the distal link. The system also includes an instrument support coupled to the distal link, wherein the instrument support has (Continued)

an orientation relative to the base in a first configuration of the support structure, and wherein the linkage mechanism maintains the orientation of the instrument support relative to the base as the support structure is moved into a second configuration in which the support structure is rotated relative to the base about the first axis and the distal link is extended from the proximal link.

24 Claims, 27 Drawing Sheets

(51) Int. Cl.
*A61B 34/37* (2016.01)
*A61B 90/50* (2016.01)

(58) Field of Classification Search
CPC .......... A61B 34/35; A61B 2017/00809; A61B 2090/371; A61B 2090/3614; A61B 2034/105; A61B 2034/2051; A61B 2034/2061; A61B 2034/2059; A61B 2090/372; A61B 90/37; A61B 2090/5025; A61B 90/50; A61B 34/70; A61B 2017/00477
See application file for complete search history.

(56) References Cited

U.S. PATENT DOCUMENTS

| | | | |
|---|---|---|---|
| 8,900,131 B2 | 12/2014 | Chopra et al. | |
| 9,107,683 B2 | 8/2015 | Hourtash et al. | |
| 2004/0035243 A1* | 2/2004 | Duval | F16F 1/12 74/589 |
| 2007/0156122 A1* | 7/2007 | Cooper | A61B 90/50 606/1 |
| 2007/0197896 A1* | 8/2007 | Moll | A61B 1/00039 600/407 |
| 2009/0030429 A1* | 1/2009 | Madhani | B25J 9/1697 606/130 |
| 2011/0071347 A1* | 3/2011 | Rogers | A61B 34/30 600/104 |
| 2011/0282359 A1* | 11/2011 | Duval | A61B 17/3423 606/130 |
| 2012/0150192 A1* | 6/2012 | Dachs, II | A61B 34/70 606/130 |
| 2013/0041509 A1 | 2/2013 | Saito et al. | |
| 2013/0325033 A1 | 12/2013 | Schena et al. | |
| 2014/0343567 A1* | 11/2014 | Morash | A61B 34/20 606/130 |
| 2015/0367519 A1* | 12/2015 | Goldberg | B25J 19/0016 16/401 |
| 2016/0242849 A9* | 8/2016 | Crawford | A61B 5/066 |
| 2016/0332312 A1* | 11/2016 | Song | B25J 19/0016 |
| 2018/0055583 A1* | 3/2018 | Schuh | A61B 34/37 |

FOREIGN PATENT DOCUMENTS

| | | |
|---|---|---|
| WO | WO-2016025465 A1 | 2/2016 |
| WO | WO-2018005680 A1 | 1/2018 |

OTHER PUBLICATIONS

International Preliminary Report on Patentability for Application No. PCT/US2018/012995, dated Jul. 25, 2019, 8 pages.

International Search Report and Written Opinion for application No. PCT/US2018/012995, dated Jun. 4, 2018, 12 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

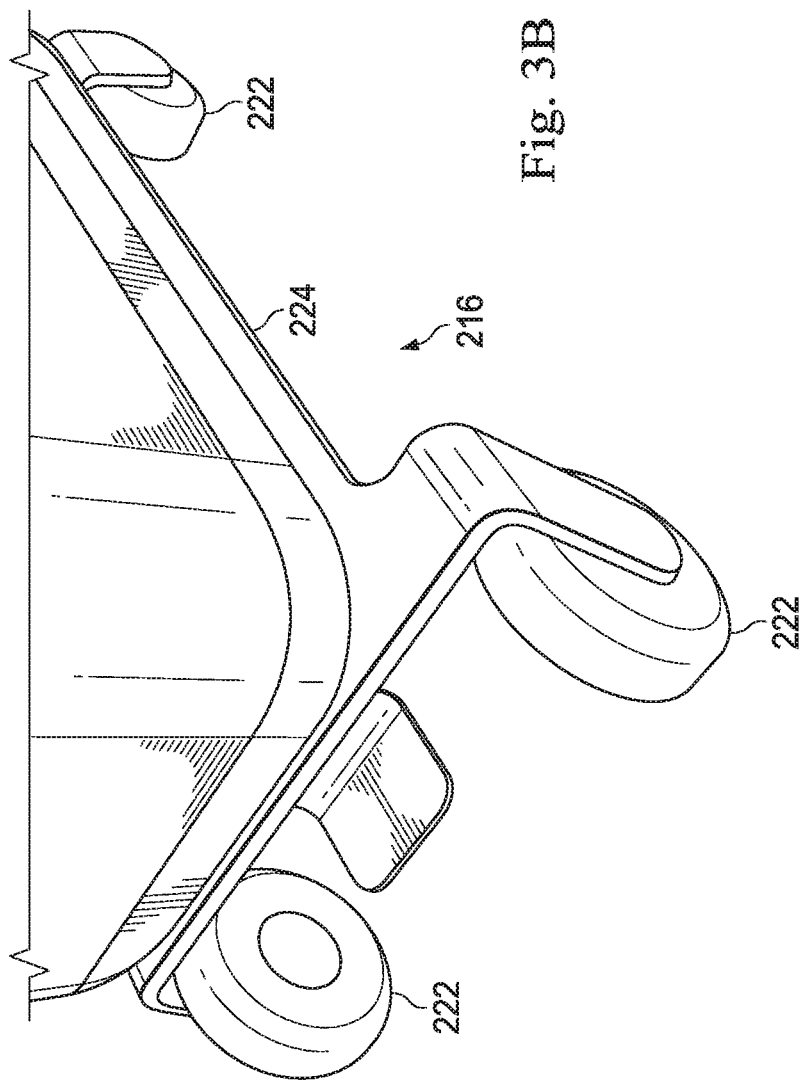

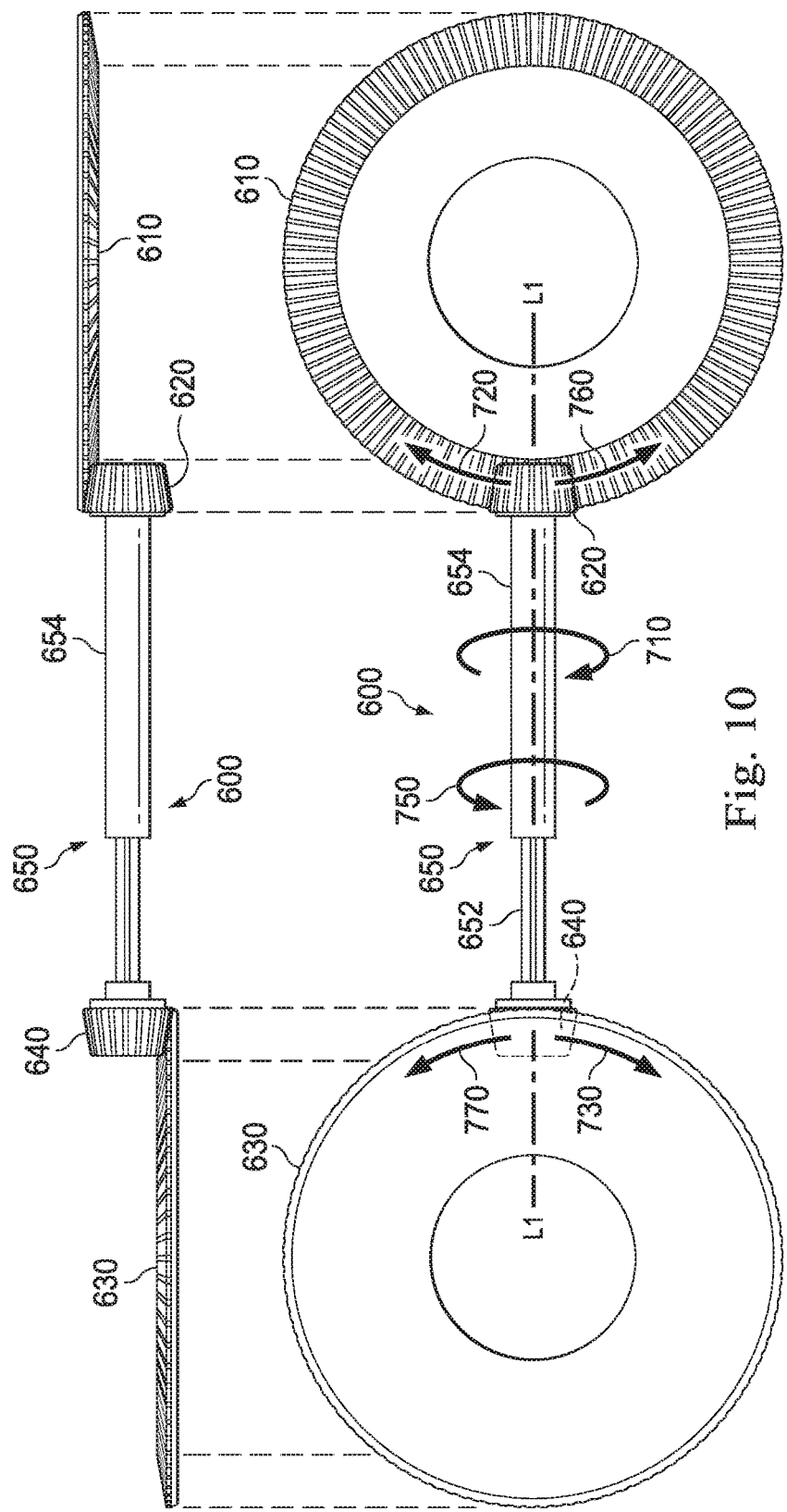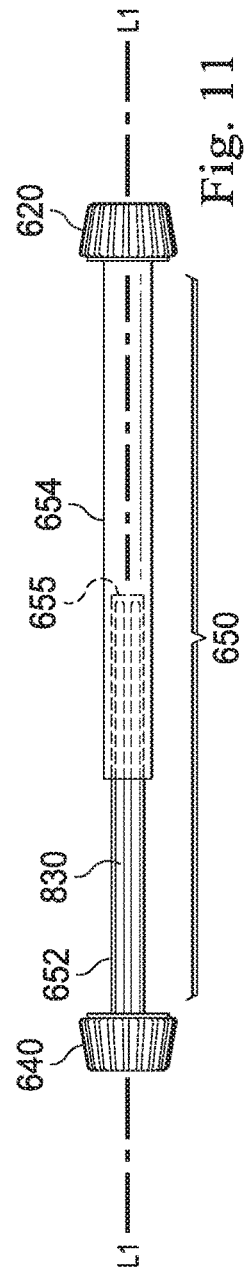

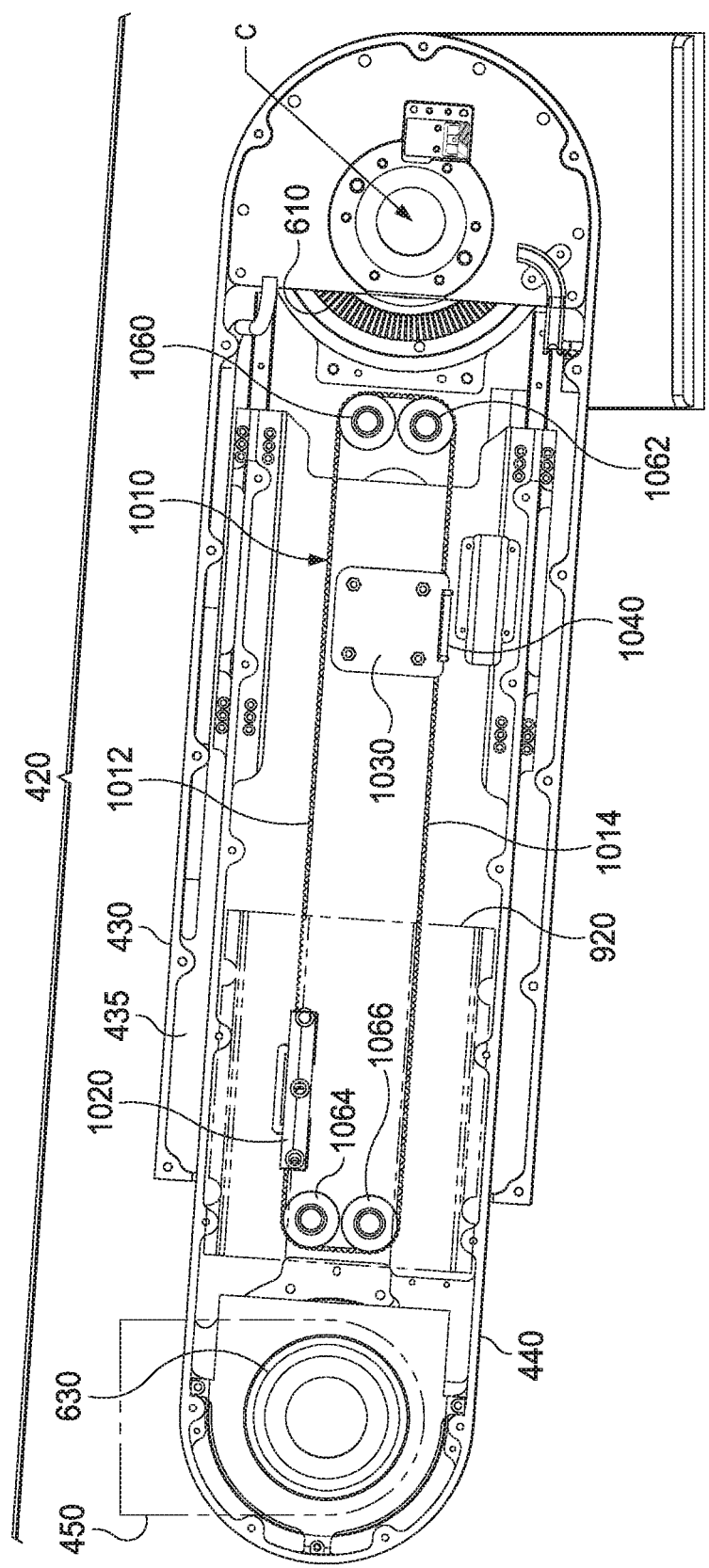

SYSTEMS AND METHODS FOR USING A ROBOTIC MEDICAL SYSTEM

RELATED APPLICATIONS

This patent application is the U.S. national phase of International Application No. PCT/US2018/012995, filed Jan. 9, 2018, which designated the U.S. and claims priority to and the benefit of the filing date of U.S. Provisional Patent Application 62/444,804, entitled "SYSTEMS AND METHODS FOR USING A ROBOTIC MEDICAL SYSTEM," filed Jan. 10, 2017, all of which are incorporated by reference herein in their entirety.

FIELD

The present disclosure is directed to systems and methods for using a medical system, and more specifically to systems and methods for controlling positioning of a medical instrument used during a minimally invasive medical procedure.

BACKGROUND

Minimally invasive medical techniques are intended to reduce an amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator (e.g., a physician) may insert minimally invasive medical instruments (including surgical, diagnostic, therapeutic, or biopsy instruments) to reach a target tissue location. One such minimally invasive technique is to use a flexible and/or steerable elongate device, such as a flexible catheter, that can be inserted into anatomic passageways and navigated toward a region of interest within the patient anatomy. Control of such an elongate device by medical personnel involves the management of several degrees of freedom including at least the management of insertion and retraction of the elongate device as well as steering of the device. In addition, different modes of operation may also be supported.

Some minimally invasive medical instruments may be teleoperated or otherwise computer-assisted. After a medical instrument is attached to a teleoperational manipulator, the manipulator may be teleoperationally or manually manipulated to adjust the instrument. When adjusting the instrument, it may be desirable to change the instrument position (e.g., vertically and/or horizontally) while maintaining a constant orientation of the instrument. For example, the direction of the instrument with respect to the ground may be maintained while the vertical or horizontal position of the instrument is adjusted. Versatile systems and methods are needed to allow instrument adjustment while maintaining instrument orientation.

SUMMARY

The embodiments of the invention are best summarized by the claims that follow the description.

Consistent with some embodiments, a medical system is provided. The system may include a support structure including a proximal link and a distal link. The system may further include a base joint coupling the proximal link of the support structure to a base, and the proximal link may be configured to rotate about a first axis associated with the base joint. The system may further include a linkage mechanism coupling the proximal link to the distal link and an instrument support coupled to the distal link. The instrument support may have an orientation relative to the base in a first configuration of the support structure. The linkage mechanism may maintain the orientation of the instrument support relative to the base as the support structure is moved into a second configuration in which the support structure is rotated relative to the base about the first axis and the distal link is extended from the proximal link.

Consistent with other embodiments, a medical system is provided. The system may include a support structure including a proximal link, a distal link, and a linkage mechanism coupling the proximal link to the distal link. The system may further include a base joint coupling the proximal link of the support structure to a base, and the proximal link may be configured to rotate about a first axis associated with the base joint. The system may further include an instrument manipulator for manipulating a medical instrument. The instrument manipulator may be coupled to the distal link, and the instrument manipulator may have an orientation relative to the base in a first configuration of the support structure. The system may further include a cart configured to support the base and a master control console comprising an input device for controlling the instrument manipulator during a medical procedure. The system may further include a plurality of monitors to display information related to the medical procedure. The linkage mechanism may maintain the orientation of the instrument manipulator relative to the base as the support structure is moved into a second configuration in which the support structure is rotated relative to the base about the first axis and the distal link is extended from the proximal link.

Consistent with other embodiments, a support structure for supporting an instrument manipulator is provided. The support structure may include a proximal link and a distal link, and the distal link may be configured to extend from the proximal link. The support structure may further include a base joint coupling the proximal link of the support structure to a base, and the proximal link may be configured to rotate about a first axis associated with the base joint. The system may further include a counterbalance mechanism. The counterbalance mechanism may include a counterweight block, which may be configured to move linearly within the support structure. The counterweight block may have a counterweight mass to counterbalance a combined mass of the support structure and the instrument manipulator as the distal link extends from the proximal link.

Consistent with other embodiments, a method includes moving a support structure from a first configuration to a second configuration. The method further includes maintaining, while moving the support structure from the first configuration to the second configuration, an orientation of an instrument manipulator coupled to a distal link of the support structure relative to a base. Other embodiments include corresponding computer systems, apparatus, and computer programs recorded on one or more computer storage devices, each configured to perform the actions of the methods.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIGS. 3A-D show exemplary features of portions of a cart according to some embodiments.

Figure 4A:
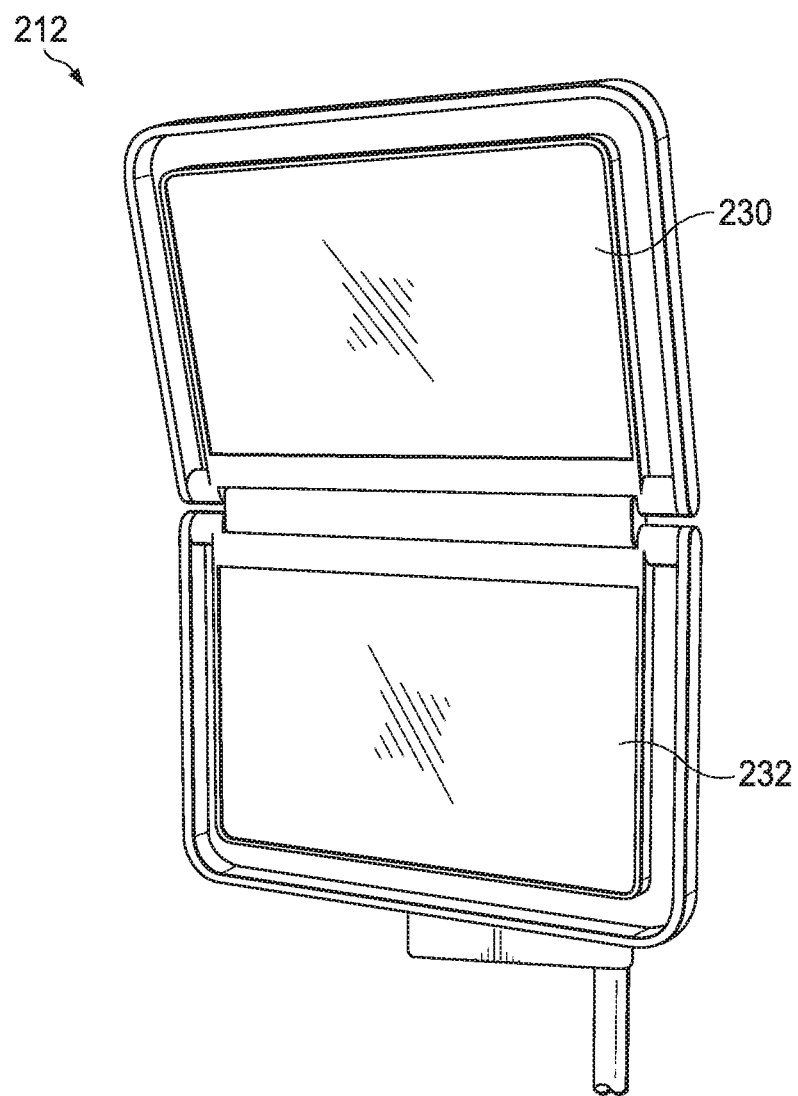
Figure 4B:
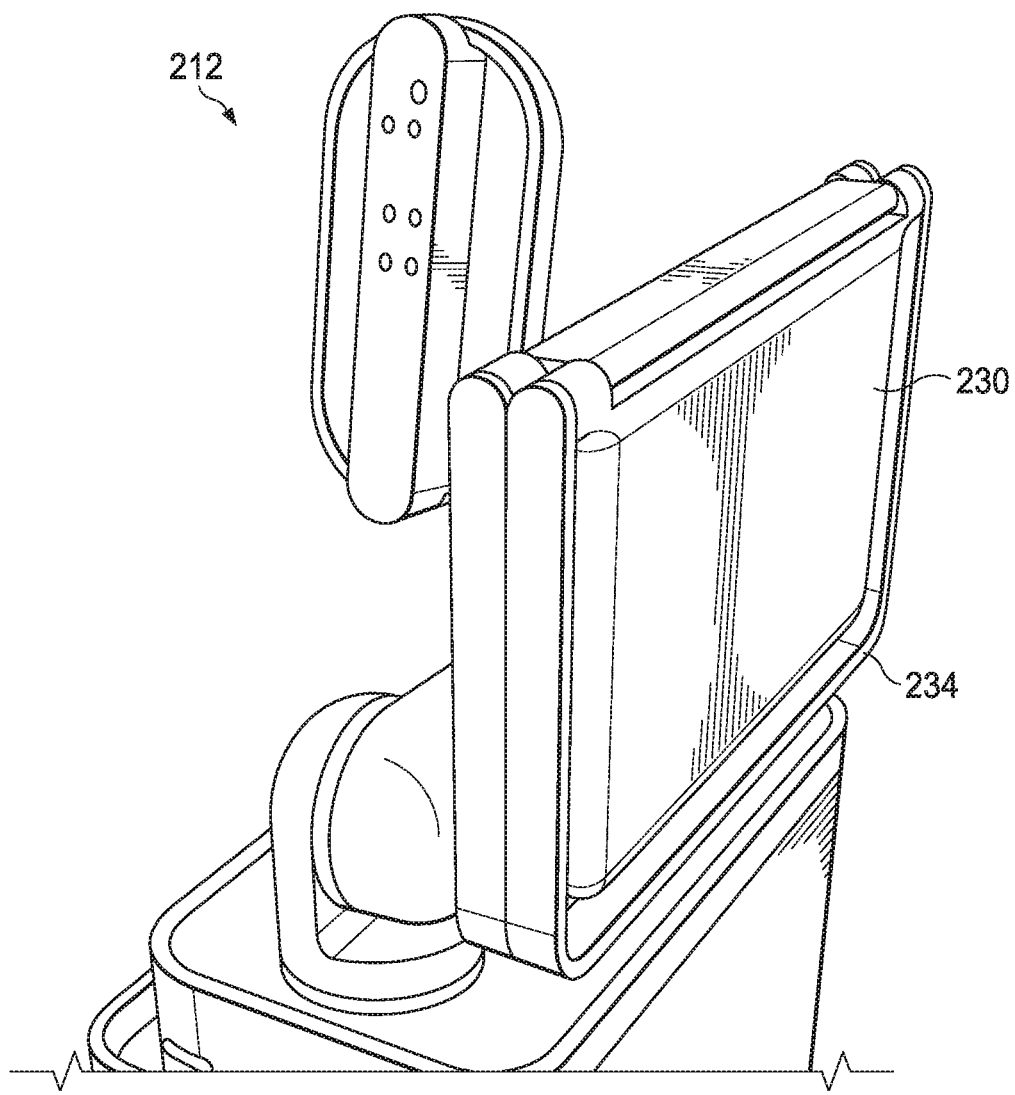

FIGS. 4A-B show exemplary features of a monitor according to some embodiments.

Figure 5A:
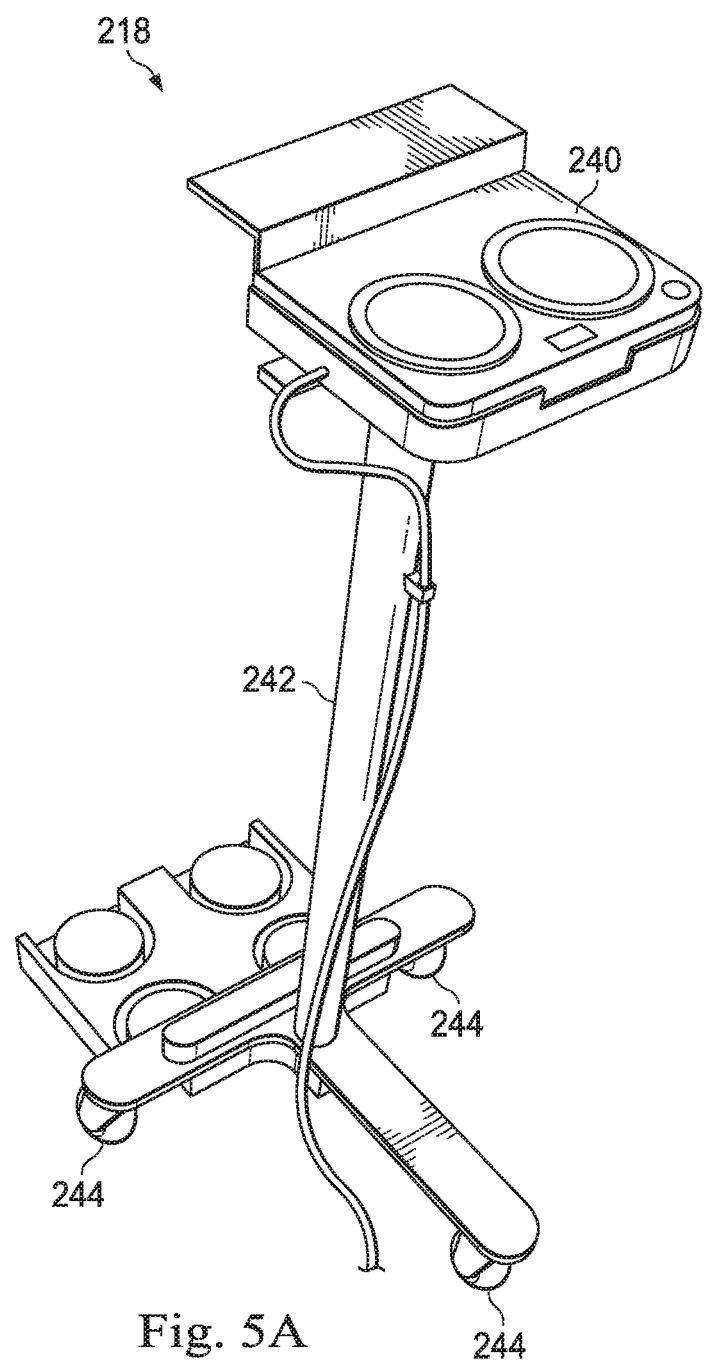
Figure 5B:
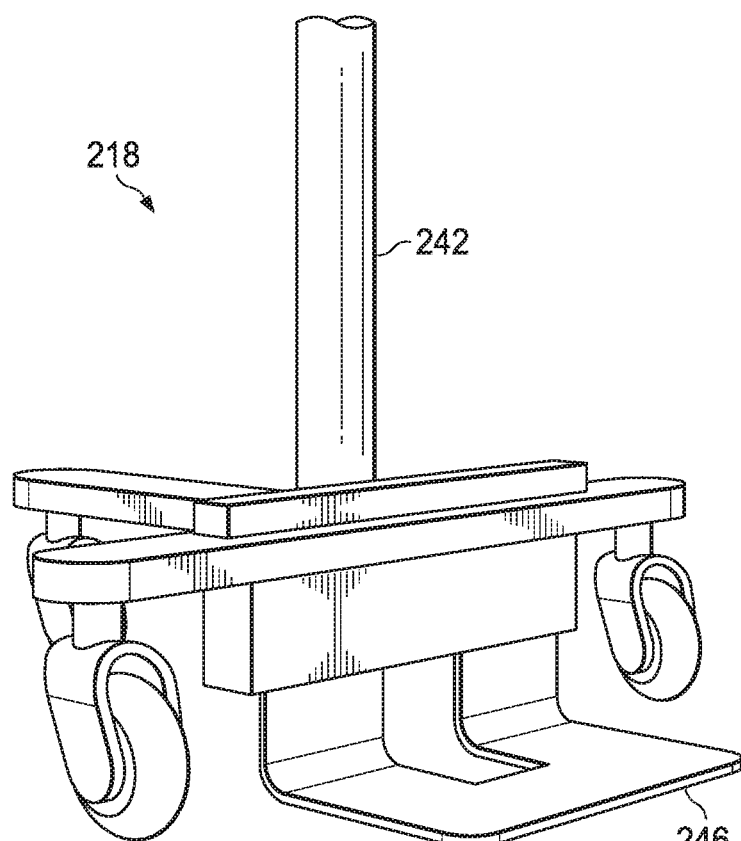
Figure 5C:
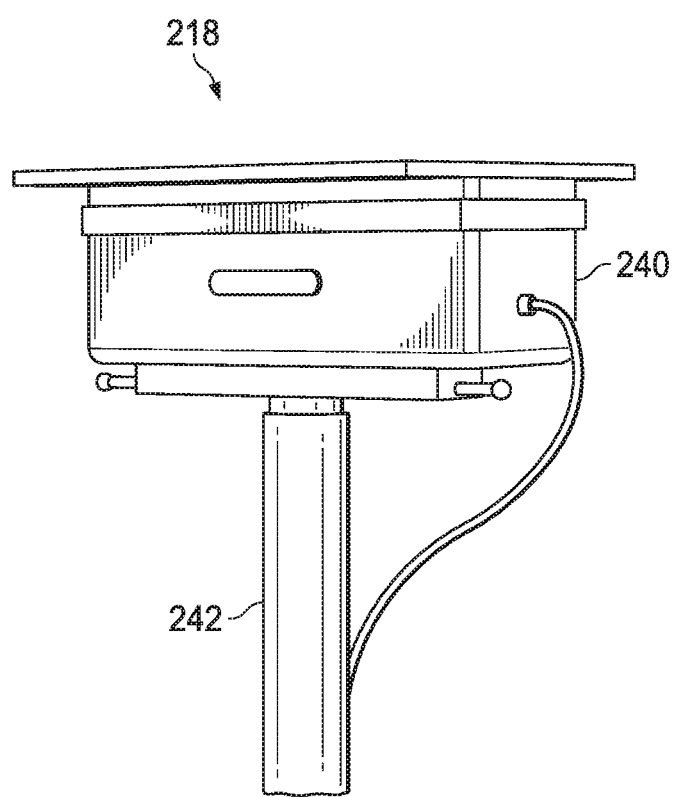

FIGS. 5A-C show exemplary features of a control console according to some embodiments.

Figure 6A:
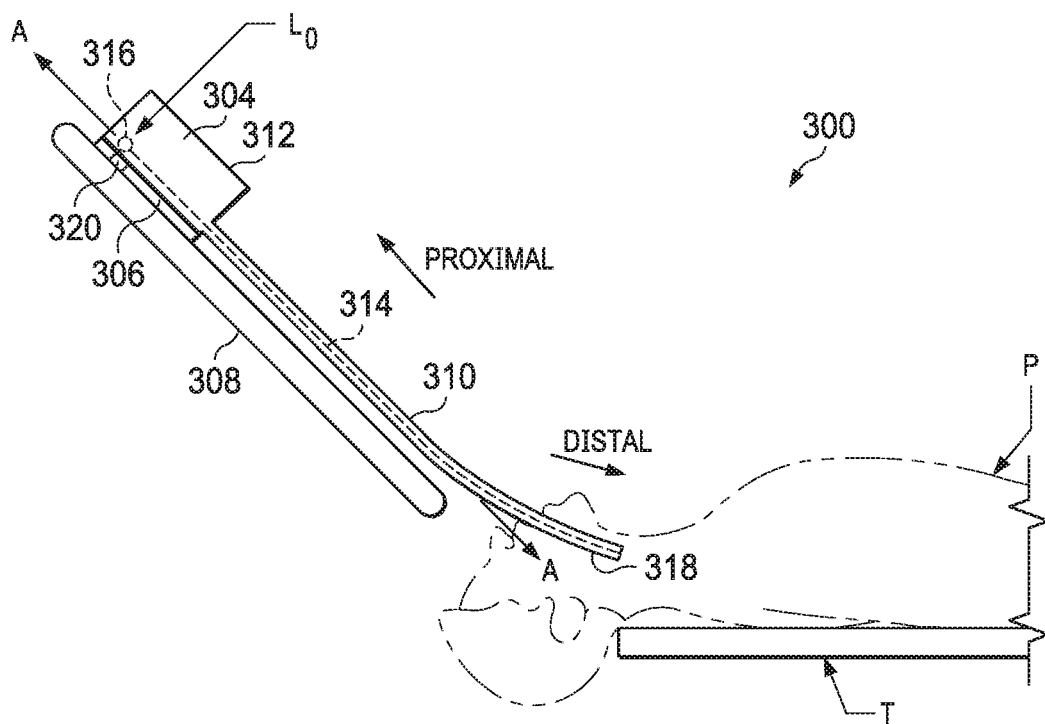
Figure 6B:
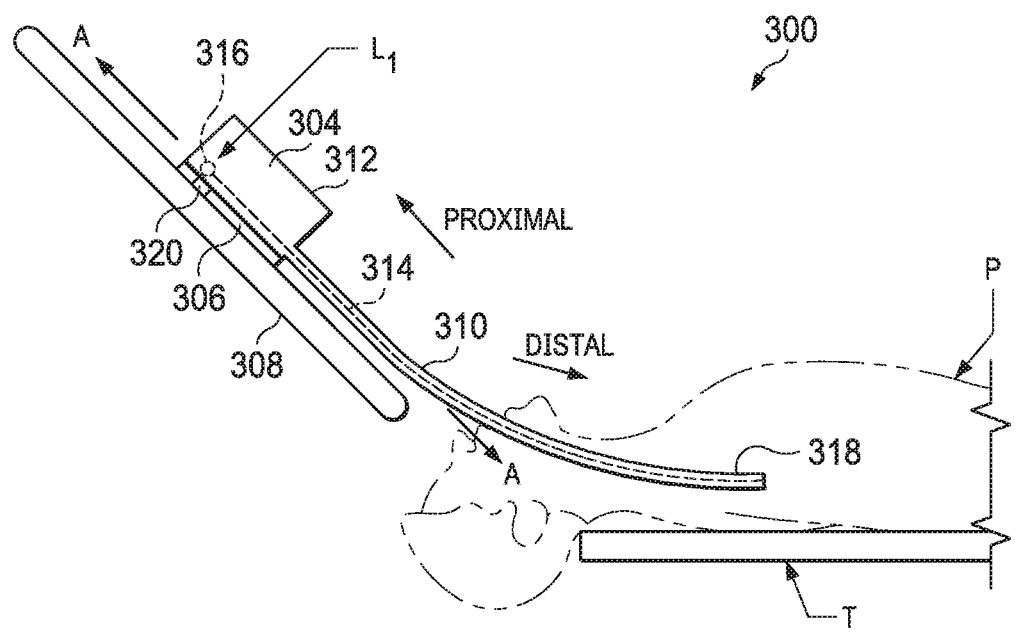

FIGS. 6A and 6B are simplified diagrams of side views of a patient coordinate space including a medical instrument mounted on an insertion assembly according to some embodiments.

Figure 7:
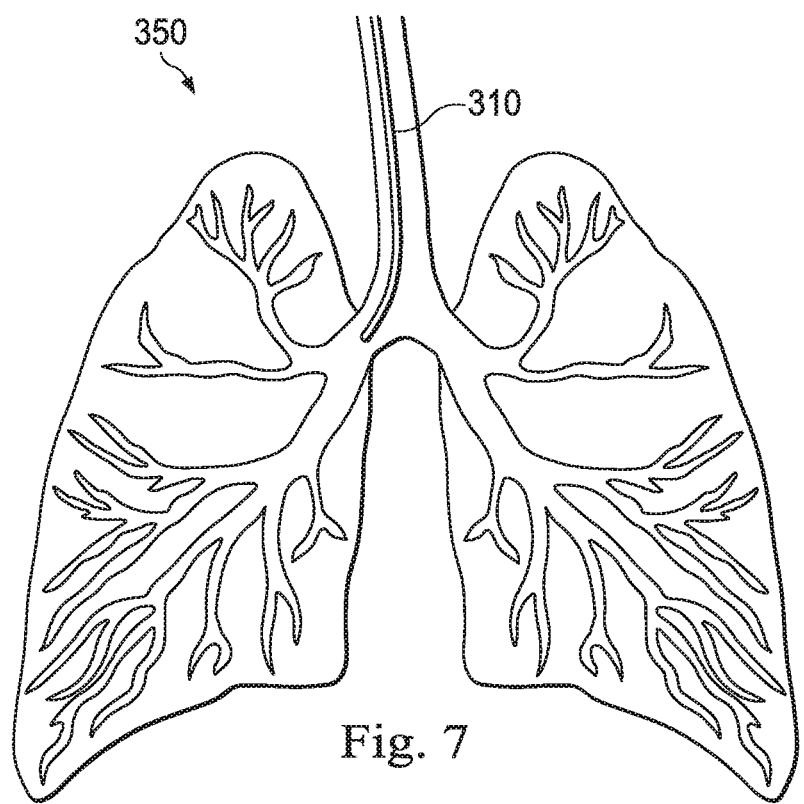

FIG. 7 shows the distal end of the medical instrument of FIG. 6A positioned within a human lung.

Figure 8A:
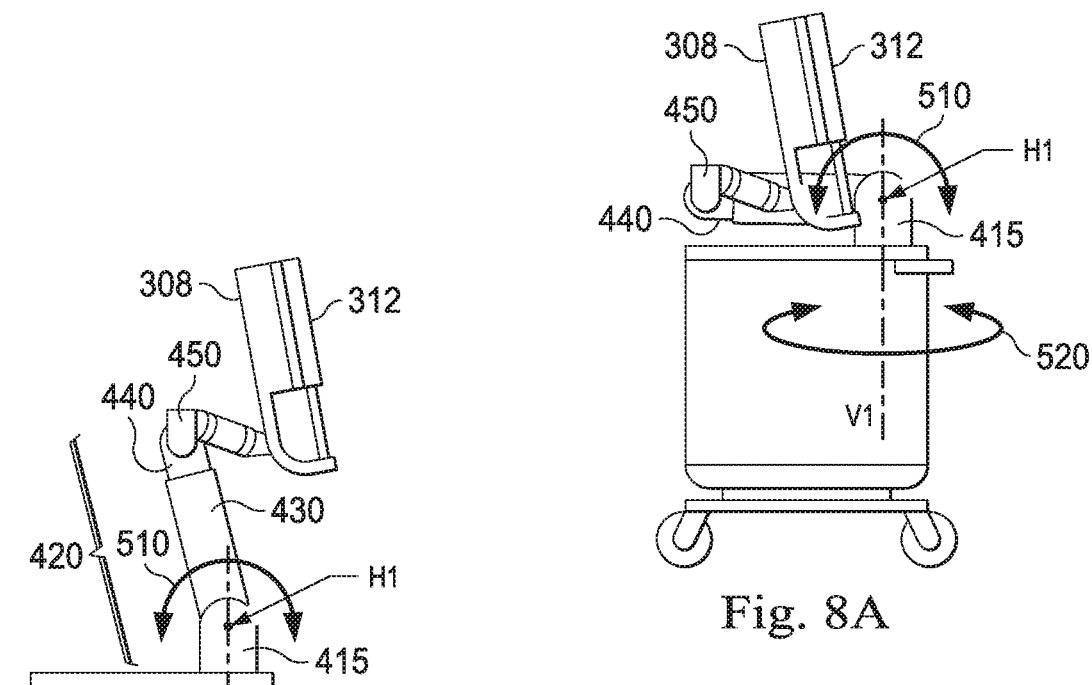
Figure 8B:
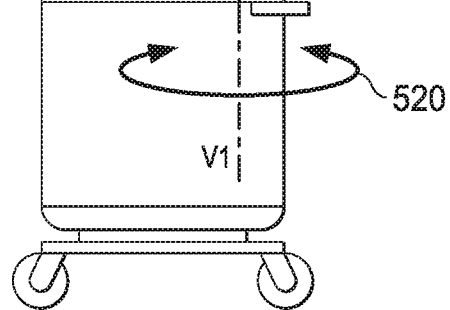
Figure 8C:
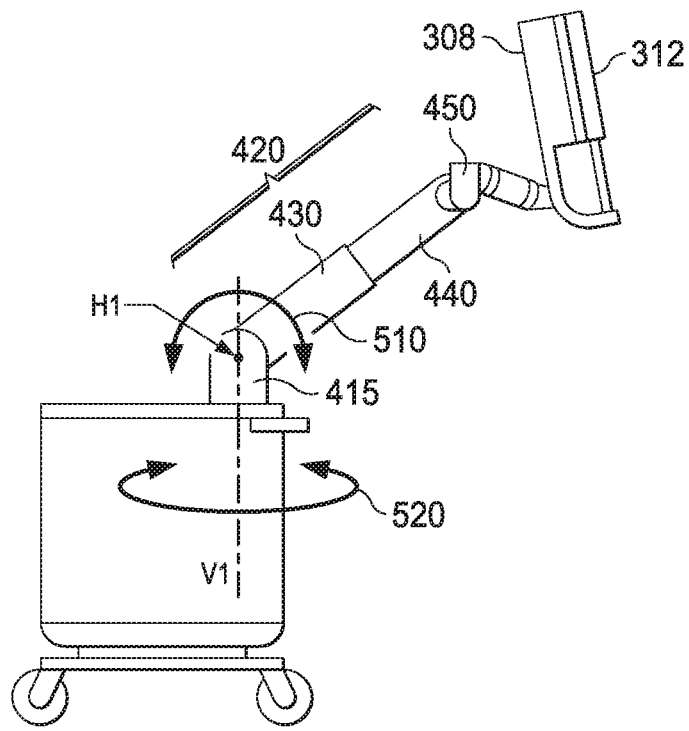

FIGS. 8A-C illustrate a proximal link positioned in exemplary configurations according to some embodiments.

Figure 9A:
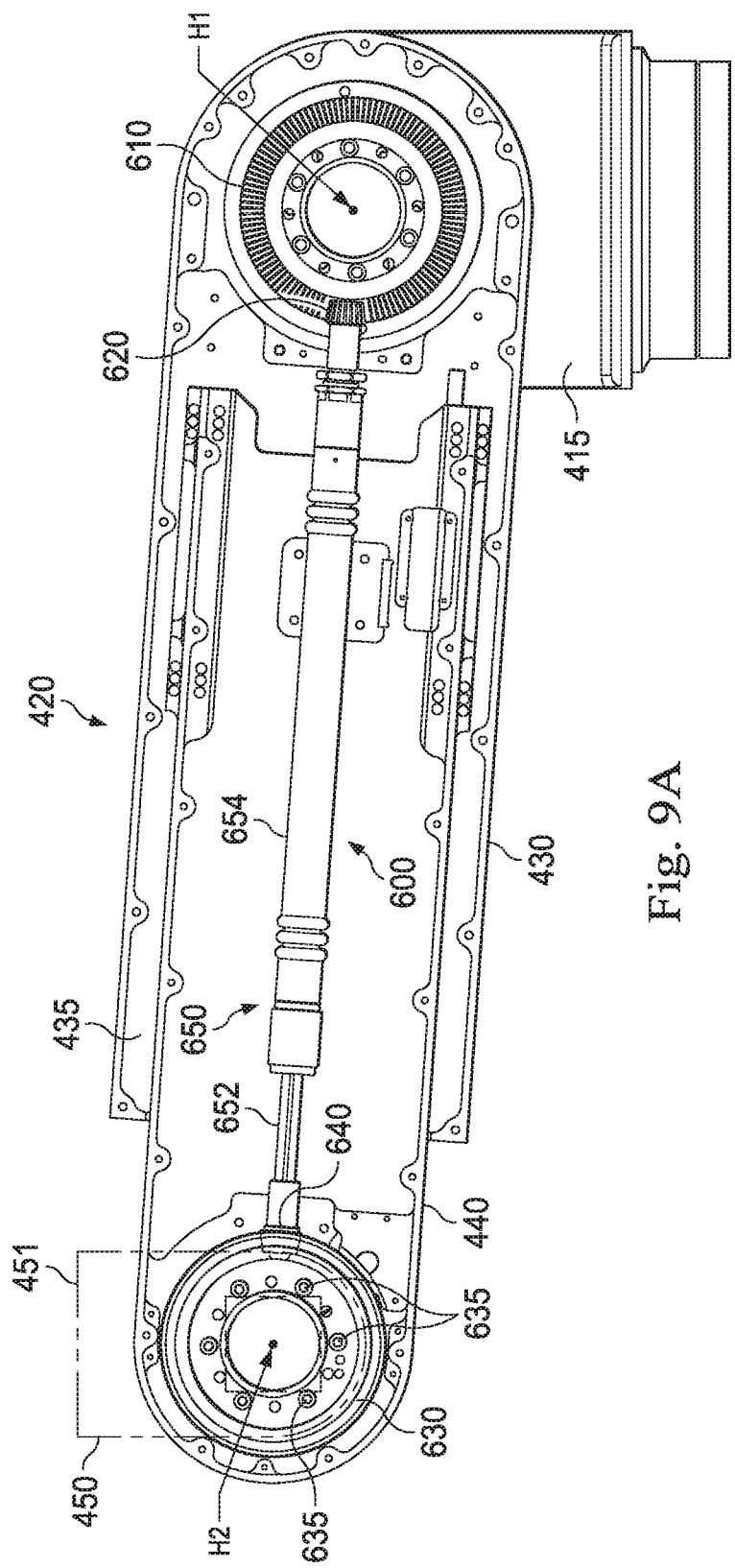

FIG. 9A illustrates an exemplary configuration of a support structure retracted within a channel of a proximal link according to some embodiments.

Figure 9B:
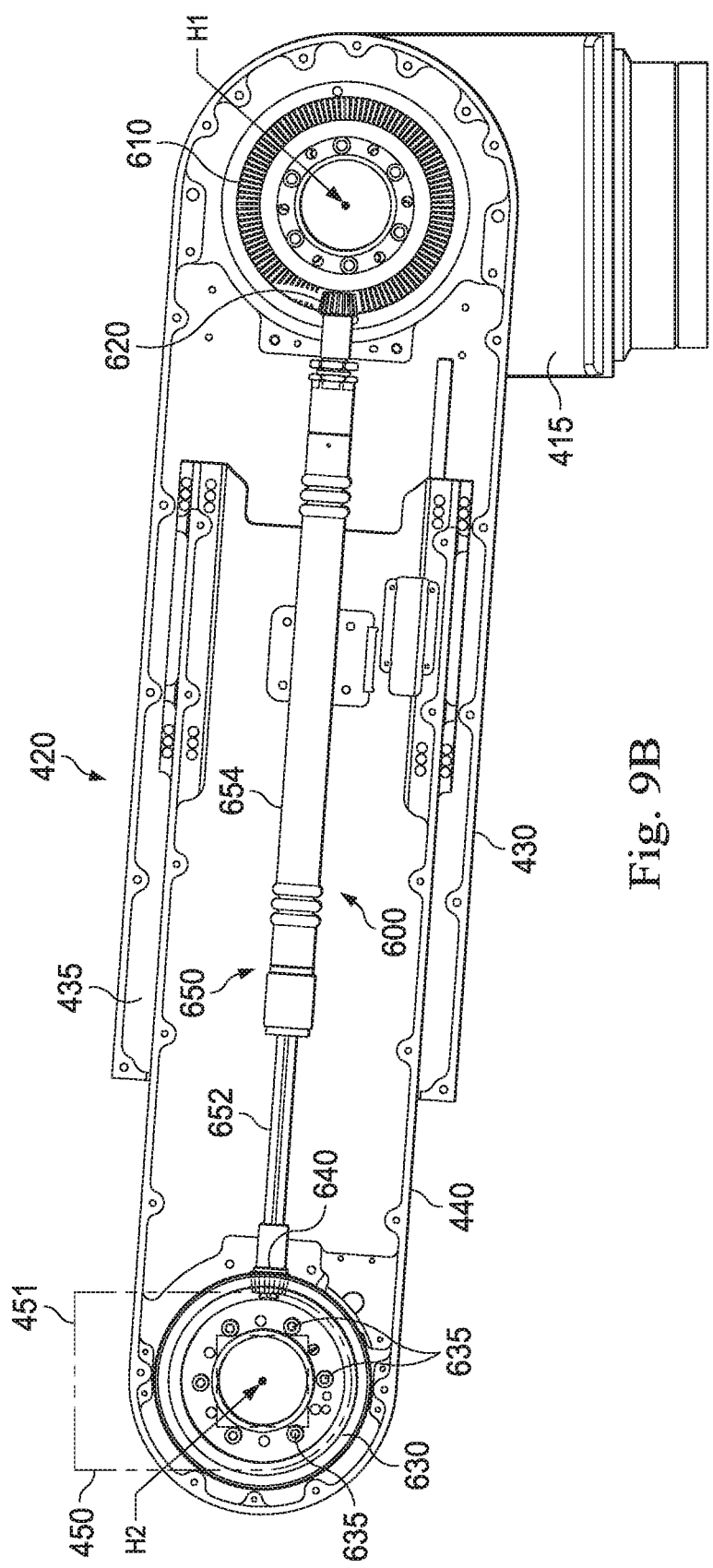

FIG. 9B illustrates an exemplary configuration of a support structure extended out from a channel of a proximal link according to some embodiments.

Figure 9C:
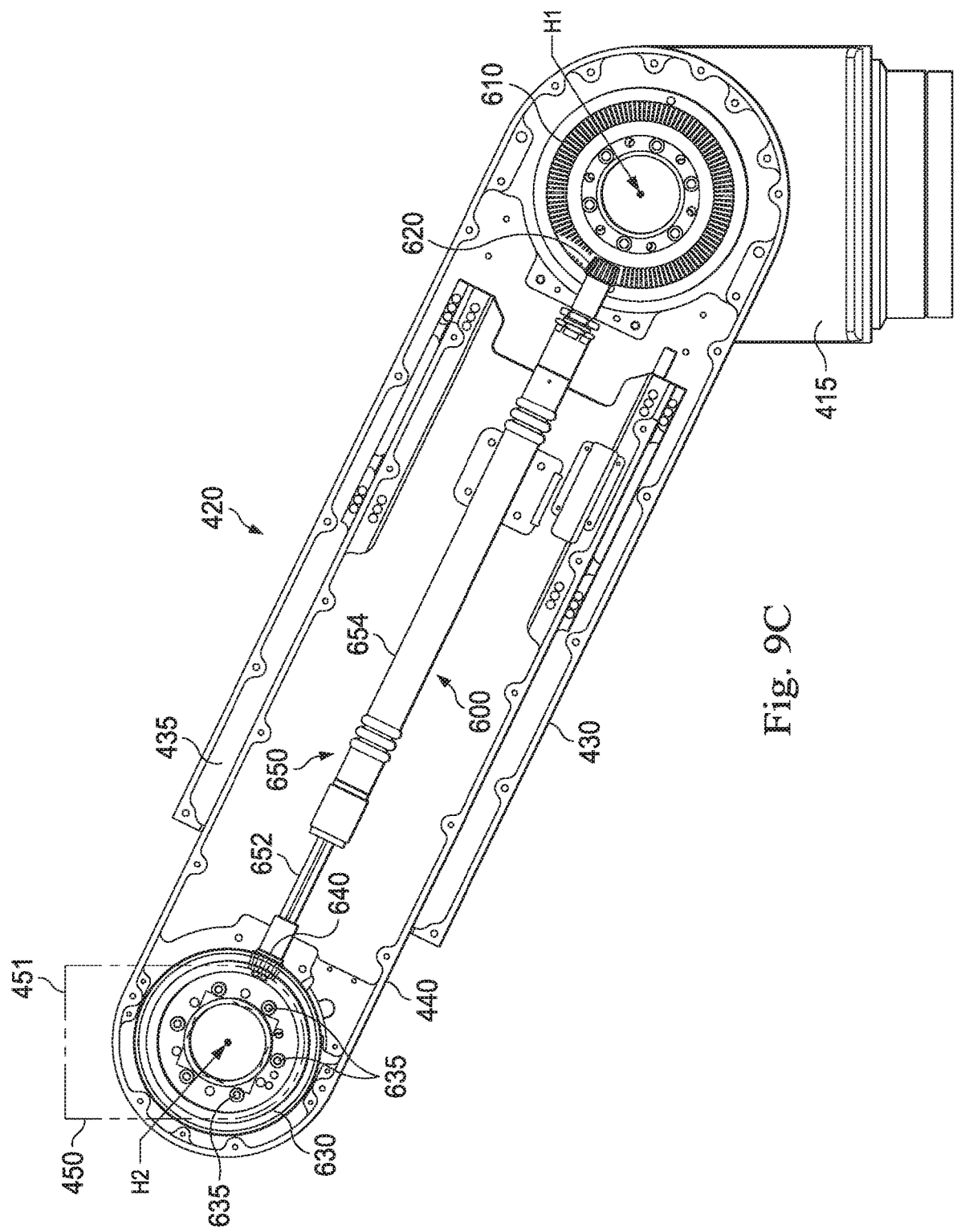

FIG. 9C illustrates an exemplary configuration of a support structure adjusted upwards according to some embodiments.

Figure 9D:
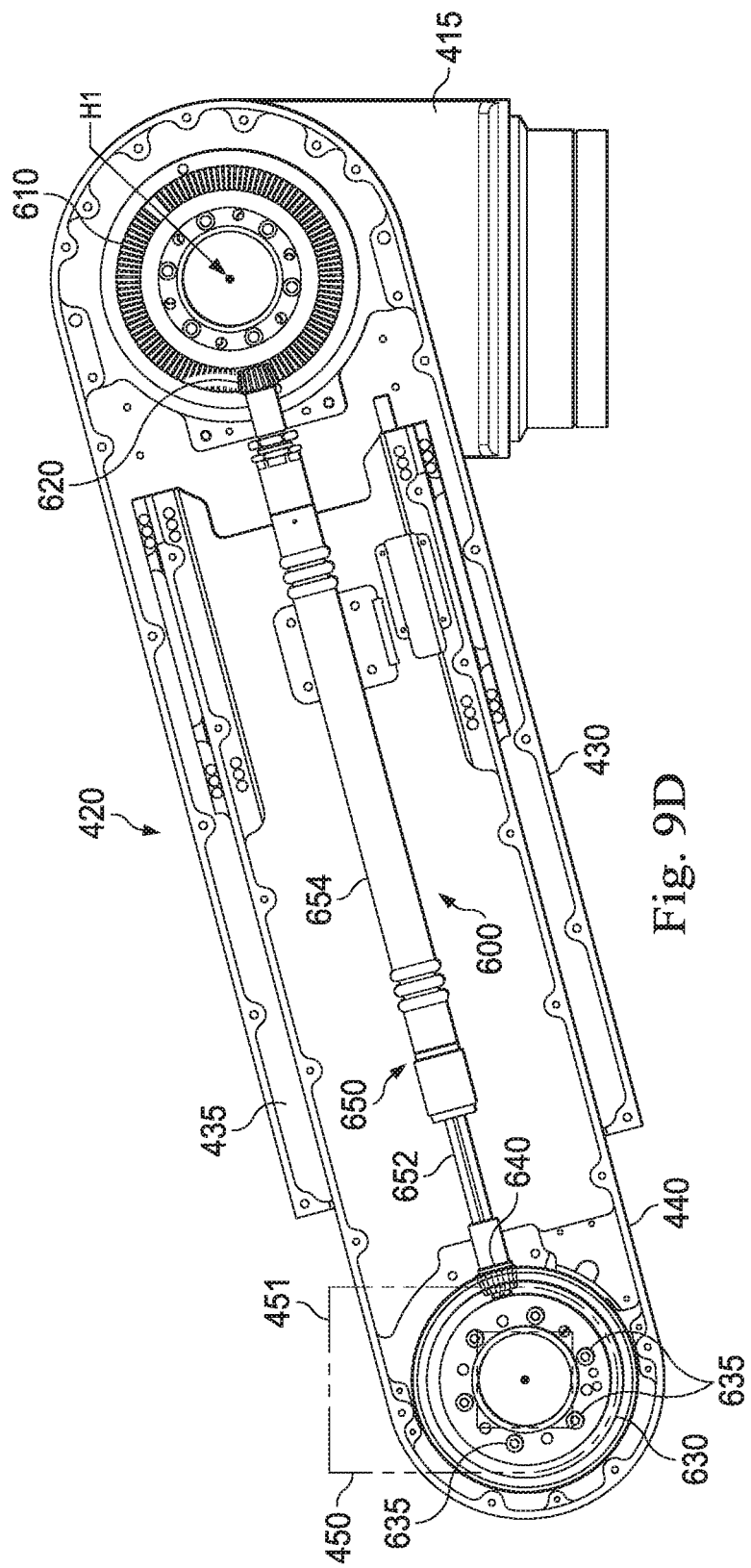

FIG. 9D illustrates an exemplary configuration of a support structure adjusted downwards according to some embodiments.

FIG. 10 illustrates an exemplary configuration of input and output bevel gears, and input and output pinions according to some embodiments.

FIG. 11 illustrates an extension mechanism according to some embodiments.

Figure 12:
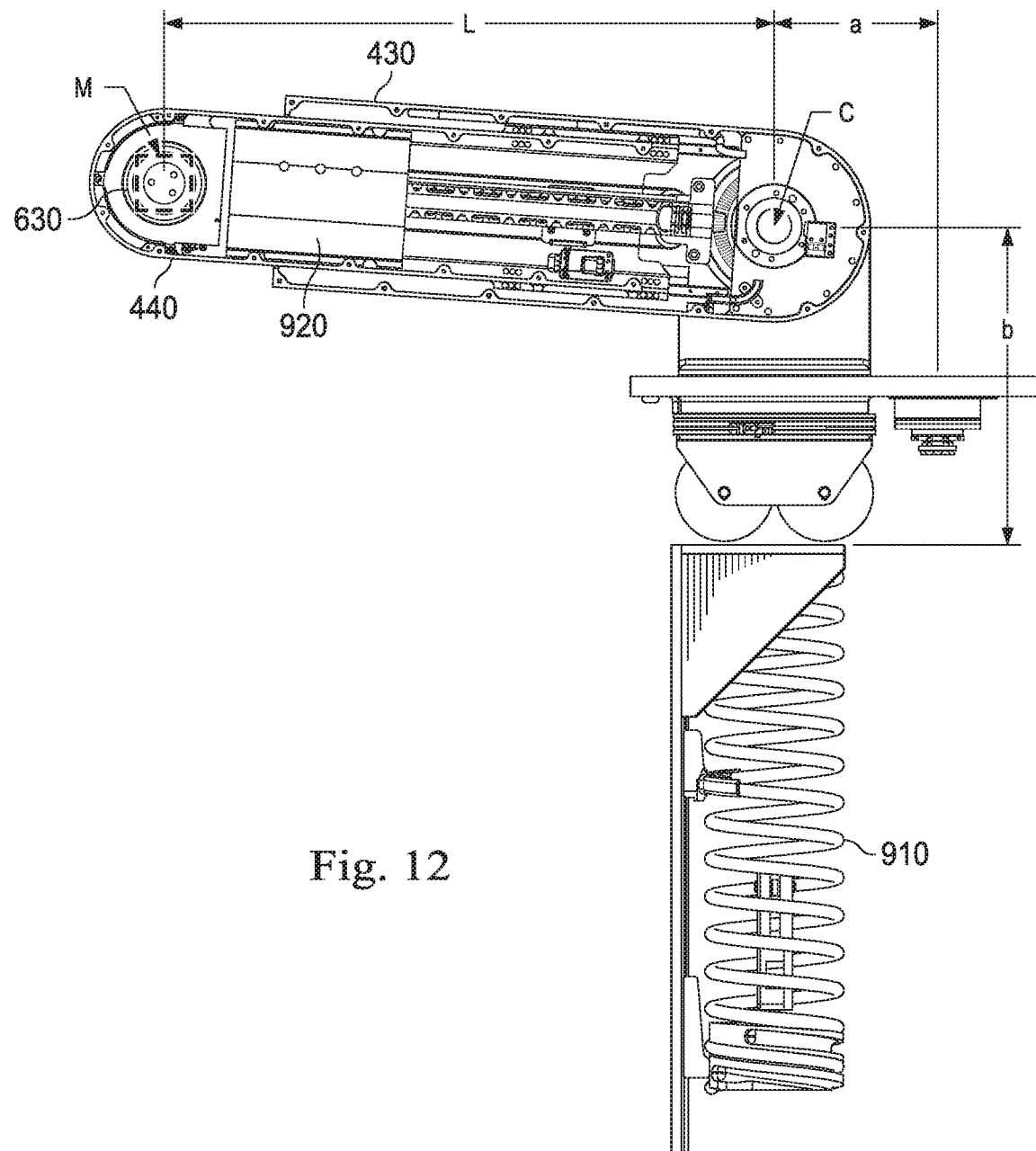

FIG. 12 illustrates an exemplary counterbalance arrangement according to some embodiments.

FIG. 13A illustrates an exemplary configuration of a support structure at equilibrium about a pivot point according to some embodiments.

Figure 13B:
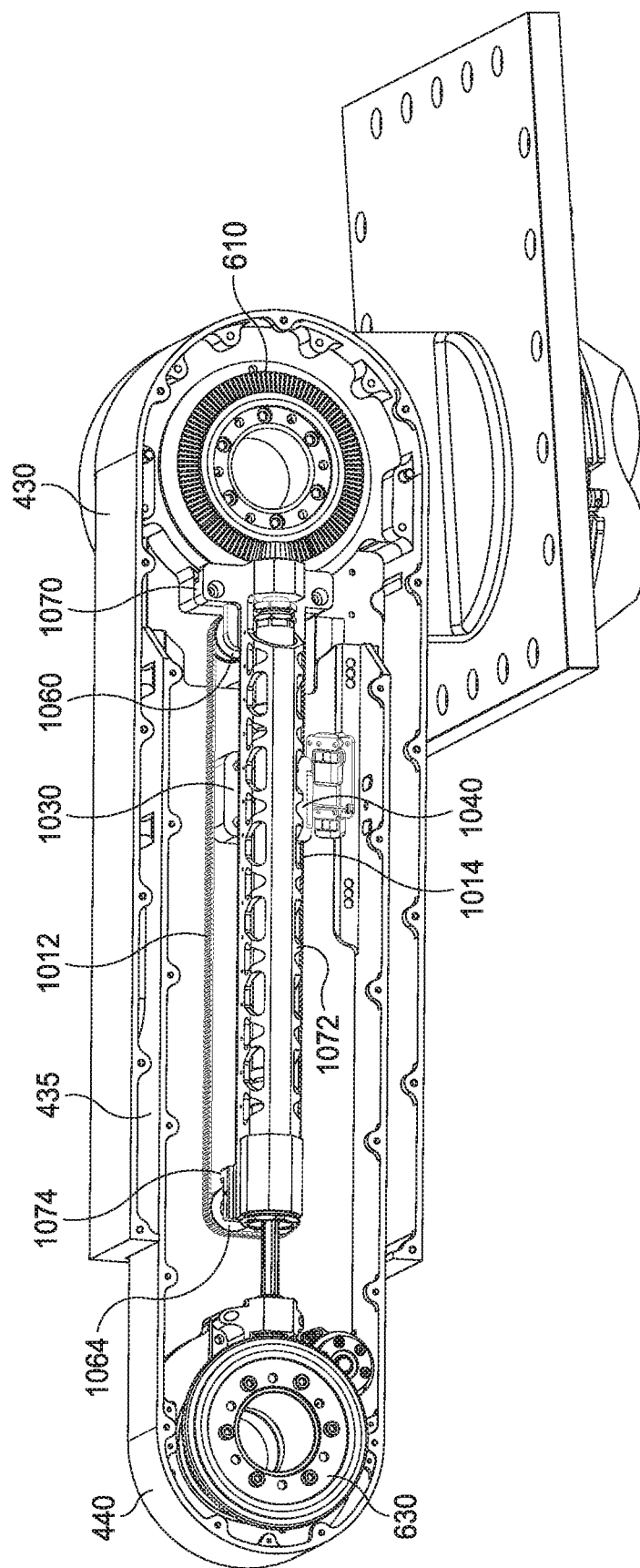

FIG. 13B illustrates an exemplary configuration of the pulley structure according to some embodiments.

Figure 14:
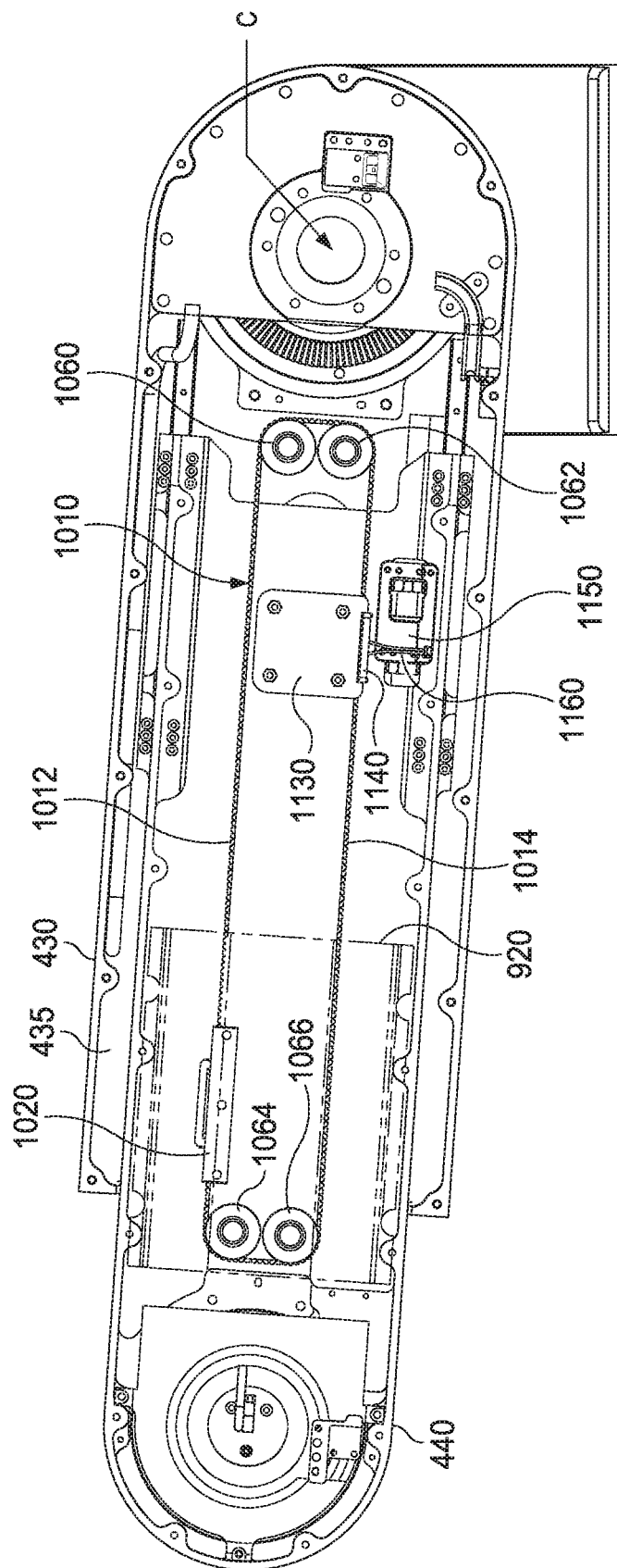

FIG. 14 illustrates another exemplary configuration of the support structure at equilibrium about the pivot point according to some embodiments.

Figure 15:
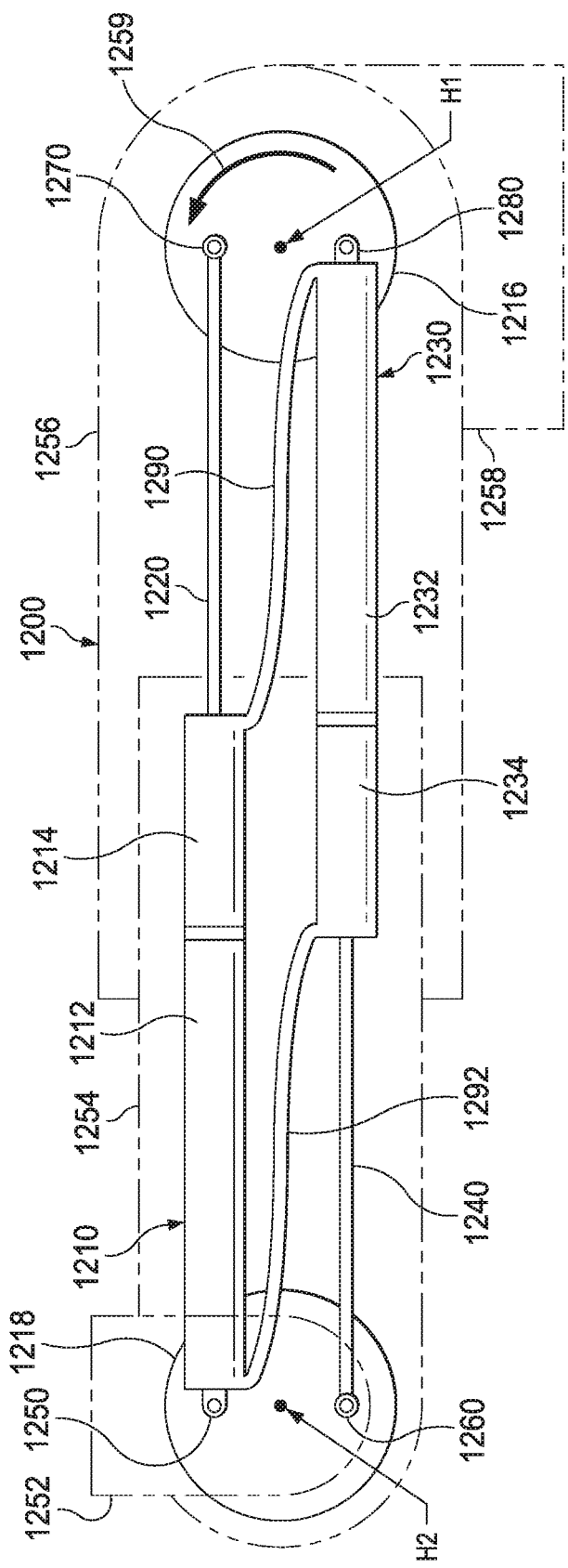

FIG. 15 illustrates another exemplary linkage mechanism including hydraulic push-pull cylinders according to some embodiments.

Figure 16:
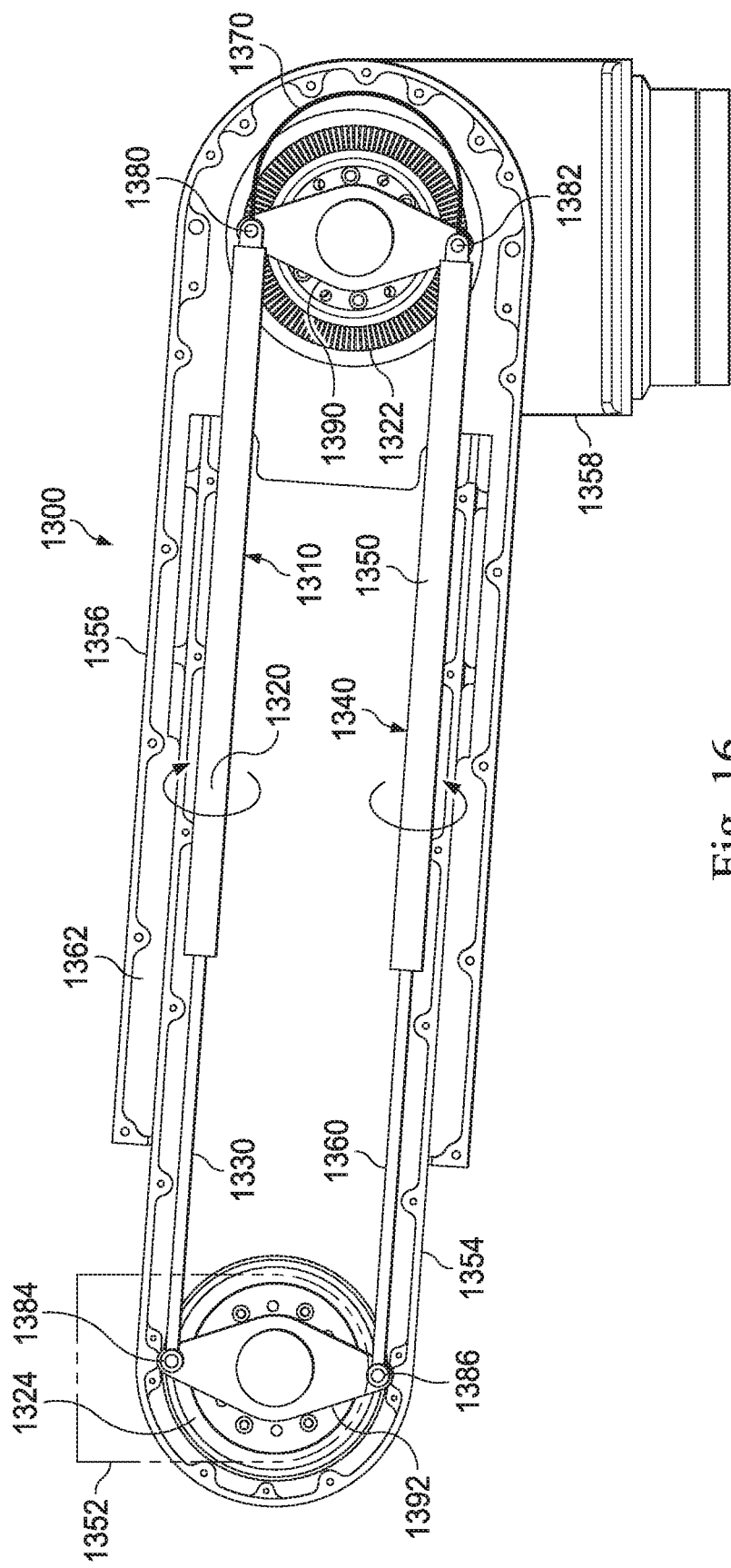

FIG. 16 illustrates another exemplary linkage mechanism including a ball-screw arrangement according to some embodiments.

Figure 17:
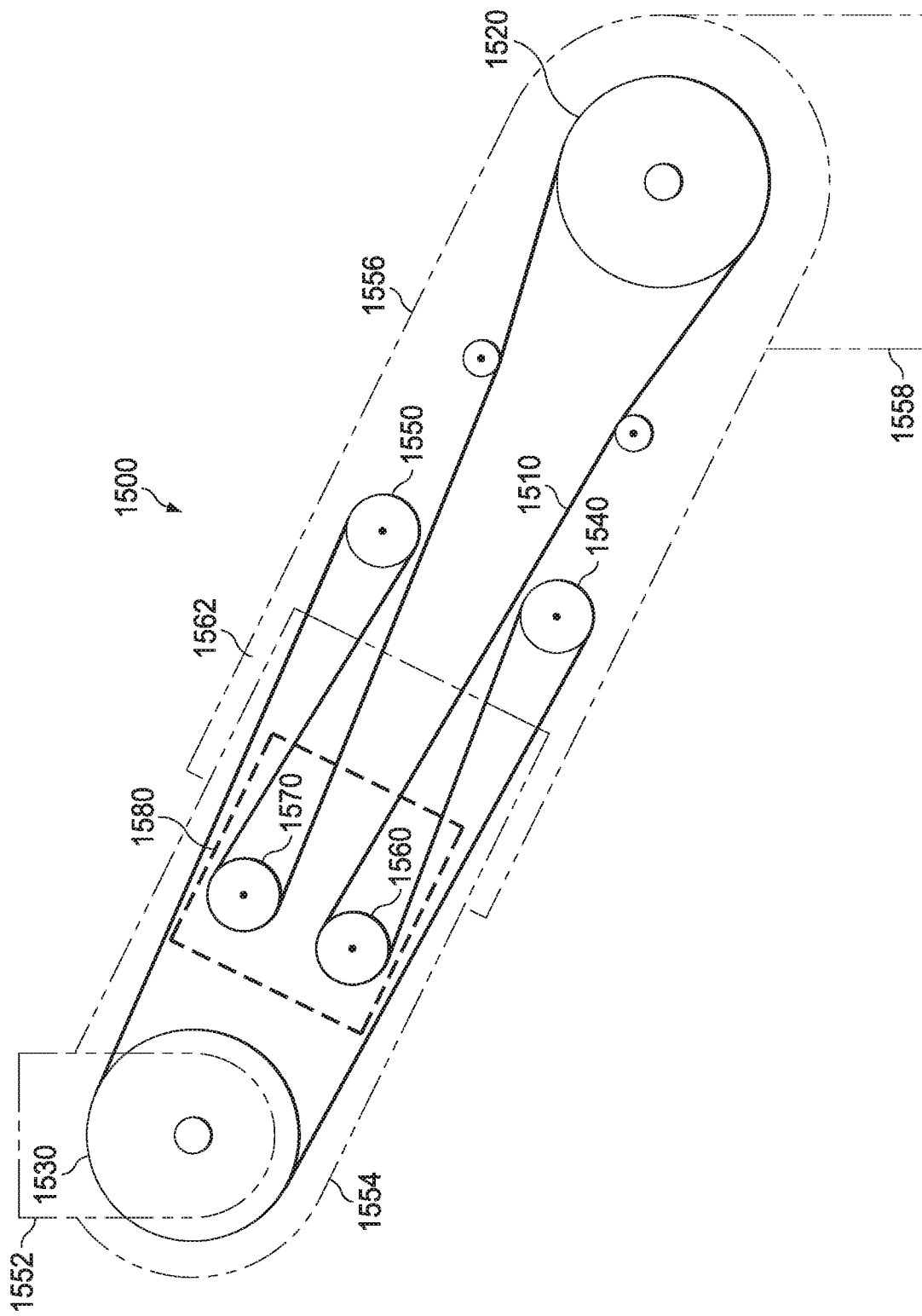

FIG. 17 illustrates another exemplary linkage mechanism including another chain and pulley arrangement according to some embodiments.

Figure 18:
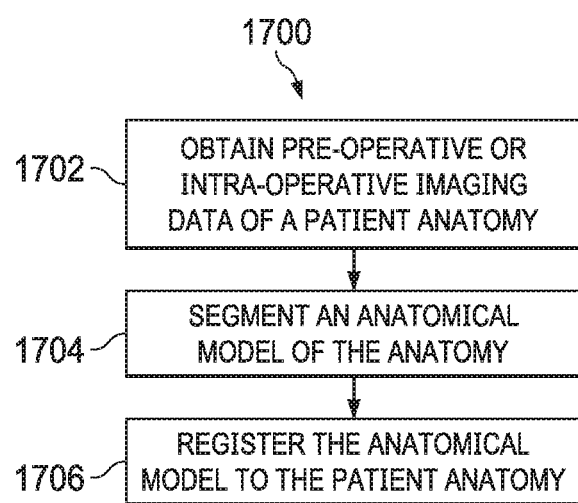

FIG. 18 is a flowchart illustrating a method used to provide guidance in an image guided surgical procedure according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
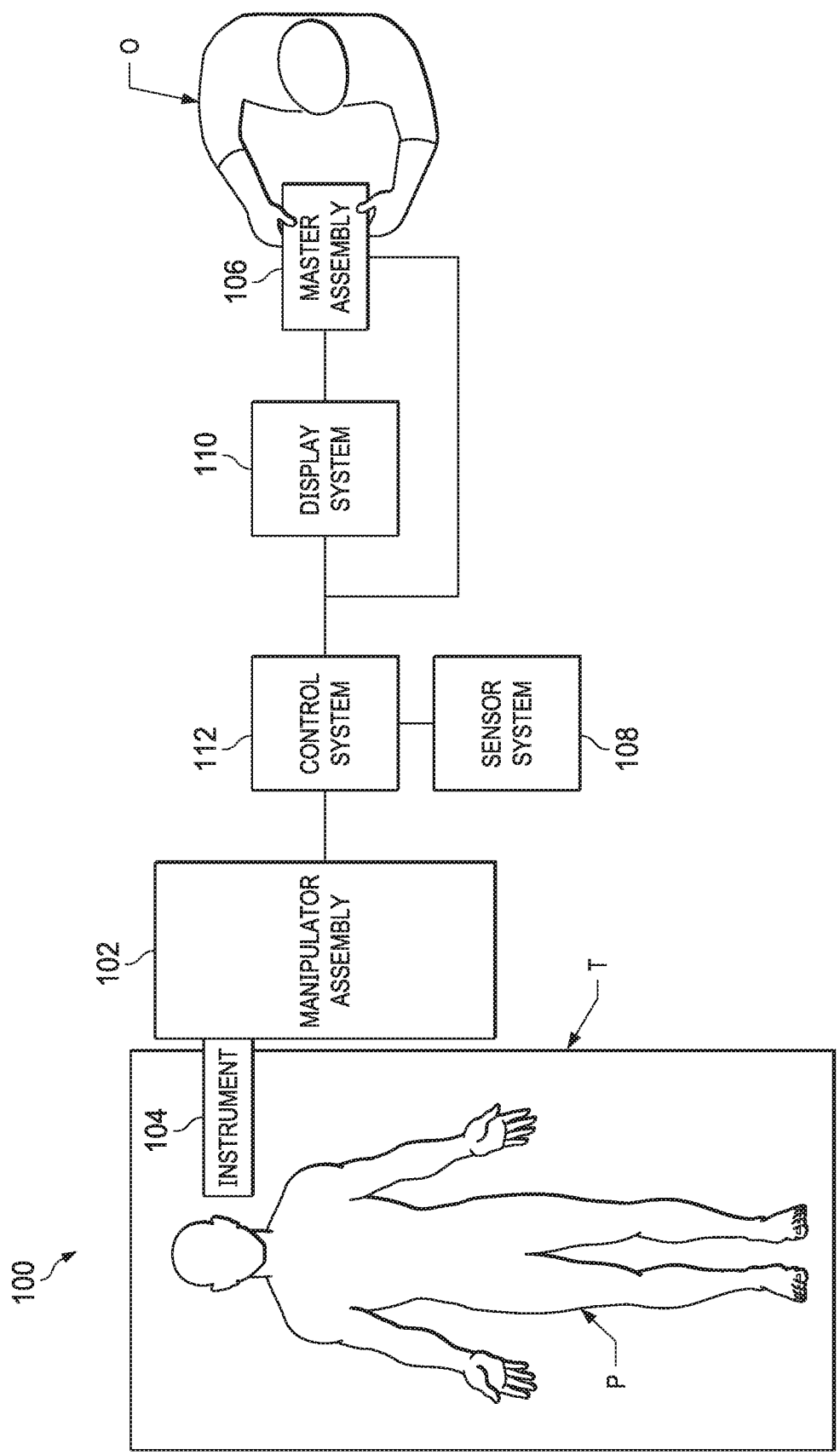
FIG. 1 is a simplified diagram of a teleoperated medical system according to some embodiments.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, teleoperated medical system 100 generally includes a manipulator assembly 102 (which may include teleoperational components) for operating a medical instrument 104 in performing various procedures on a patient P. Manipulator assembly 102 is mounted to or placed near an operating table T. A master assembly 106 allows an operator O (e.g., a surgeon, a clinician, or a physician as illustrated in FIG. 1) to view the interventional site and to control manipulator assembly 102.

Master assembly 106 may be located at a physician's console which is usually located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling medical instrument 104 the control devices may be provided with the same degrees of freedom as the associated medical instrument 104. In this manner, the control devices provide operator O with telepresence or the perception that the control devices are integral with medical instruments 104. In some embodiments, the master assembly 106 may include a master control console (MCC) 40 and a master control stand 42 (which will be discussed further in FIGS. 5A-C).

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Manipulator assembly 102 supports medical instrument 104 and may include a manipulator support assembly (as described in detail below) which has a kinematic structure of one or more non-servo controlled links (e.g., one or more links that may be manually positioned and locked in place, generally referred to as a set-up structure). The manipulator assembly 102 may also include a flexible instrument manipulator (as described in detail below) which may include an instrument carriage that travels along an insertion stage. The flexible instrument manipulator may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104 (which may, in some embodiments, be a catheter system).

Teleoperated medical system 100 also includes a display system 110 for displaying an image or representation of the surgical site and medical instrument 104 generated by subsystems of sensor system 108. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or operator O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly (which may be a teleoperational manipulator assembly) may be used with medical instrument 104 to image the surgical site. In some examples, the endoscope may include one or more mechanisms for cleaning one or more lenses of the endoscope when the one or more lenses become partially and/or fully obscured by fluids and/or other materials encountered by the endoscope. In some examples, the one or more cleaning mechanisms may optionally include an air and/or other gas delivery system that is usable to emit a puff of air and/or other gasses to blow the one or more lenses clean. Examples of the one or more cleaning mechanisms are discussed in more detail in International Publication No. WO/2016/025465 (filed Aug. 11, 2016) (disclosing "Systems and Methods for Cleaning an Endoscopic Instrument"), which is incorporated by reference herein in its entirety. The visualization system may be implemented as hardware, firmware, software, or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of an operator that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including, e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one manipulator assembly and/or more than one master assembly. The exact number of manipulator assemblies will depend on the surgical procedure and the space constraints within the operating room, among other factors. Master assembly 106 may be collocated or they may be positioned in separate locations. Multiple master assemblies allow more than one operator to control one or more manipulator assemblies in various combinations.

Figure 2:
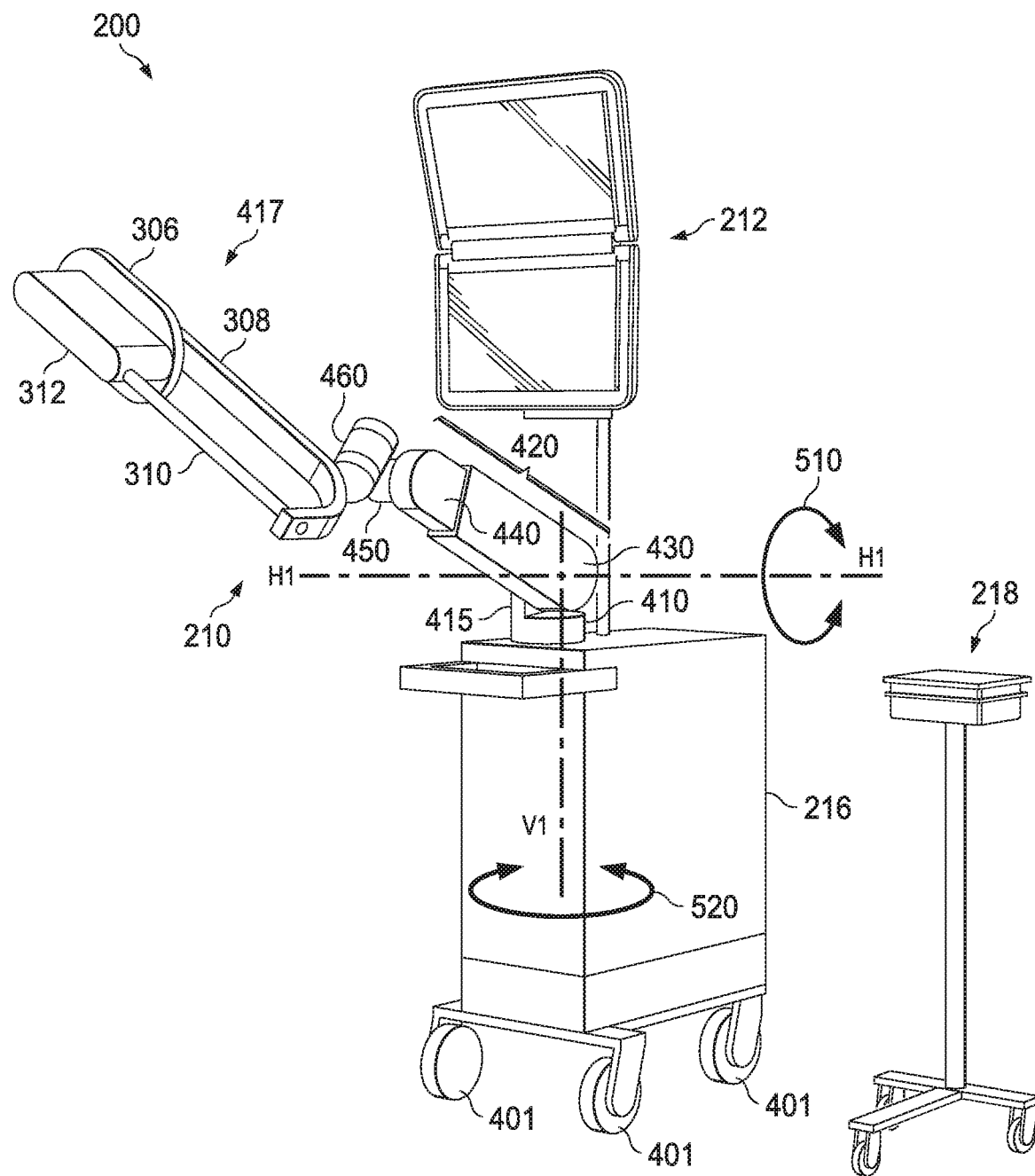
FIG. 2 shows an exemplary medical system as an embodiment of the teleoperated medical system of the present disclosure.

FIG. 2 illustrates a teleoperational medical system 200, as an embodiment of the teleoperated medical system 100. The teleoperational medical system 200 can include a master control 218, which may be used as or in conjunction with the master assembly 106. The teleoperational medical system 200 further includes a manipulator assembly 210 (e.g., a manipulator assembly 102) supported on a cart 216. The system 200 also includes a plurality of monitors 212 that may be used as the display system 110.

Figure 3A:
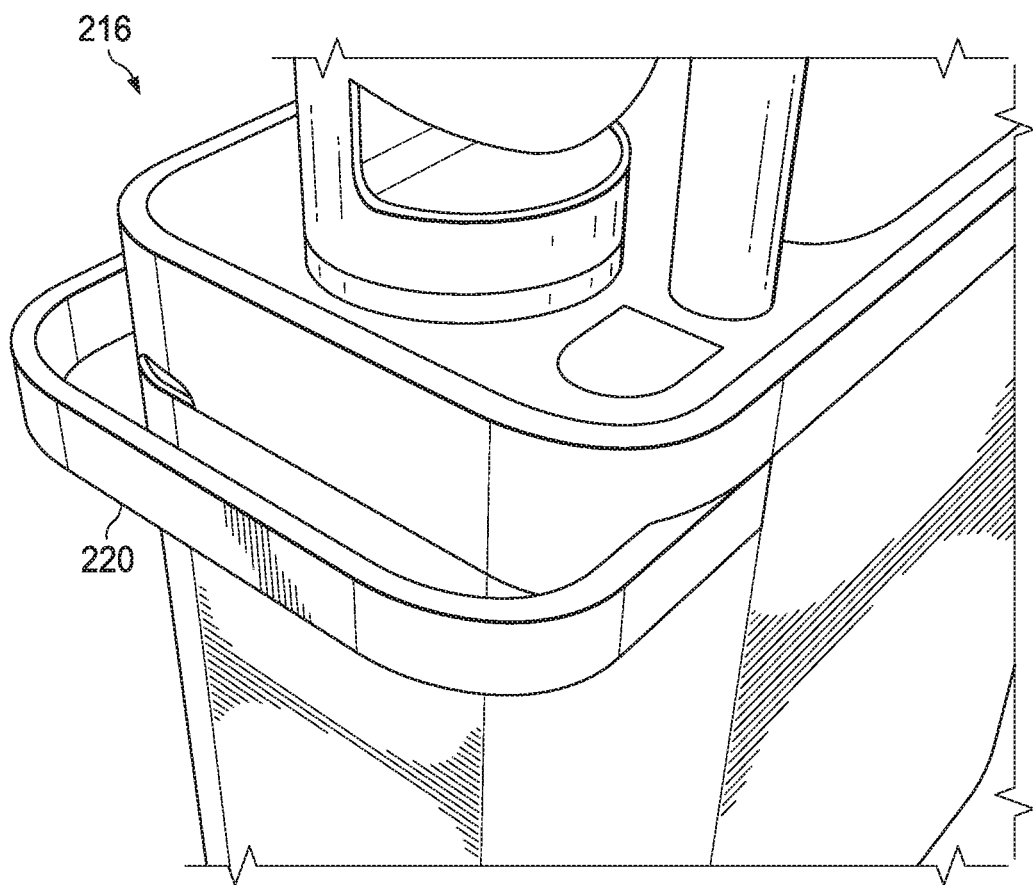
Figure 3C:
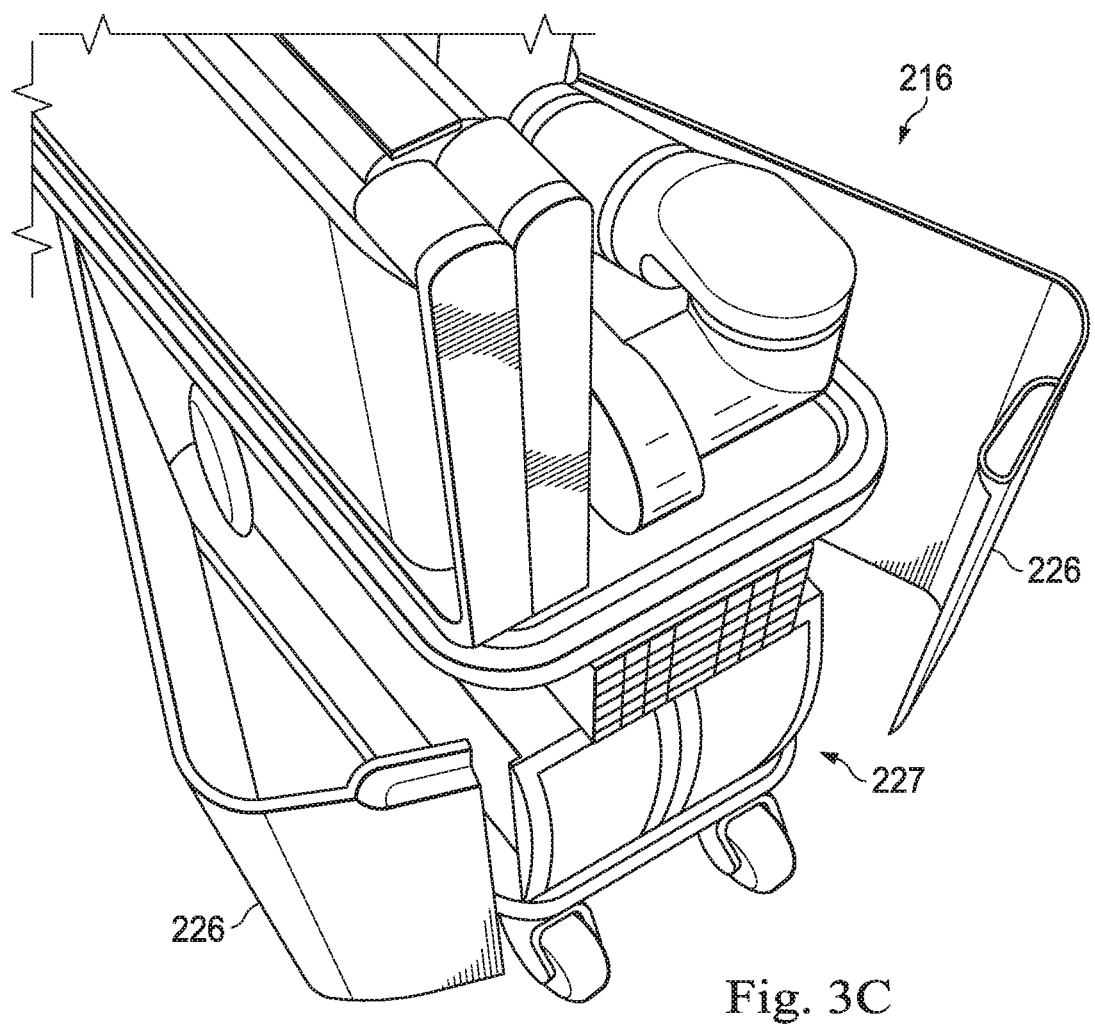
Figure 3D:
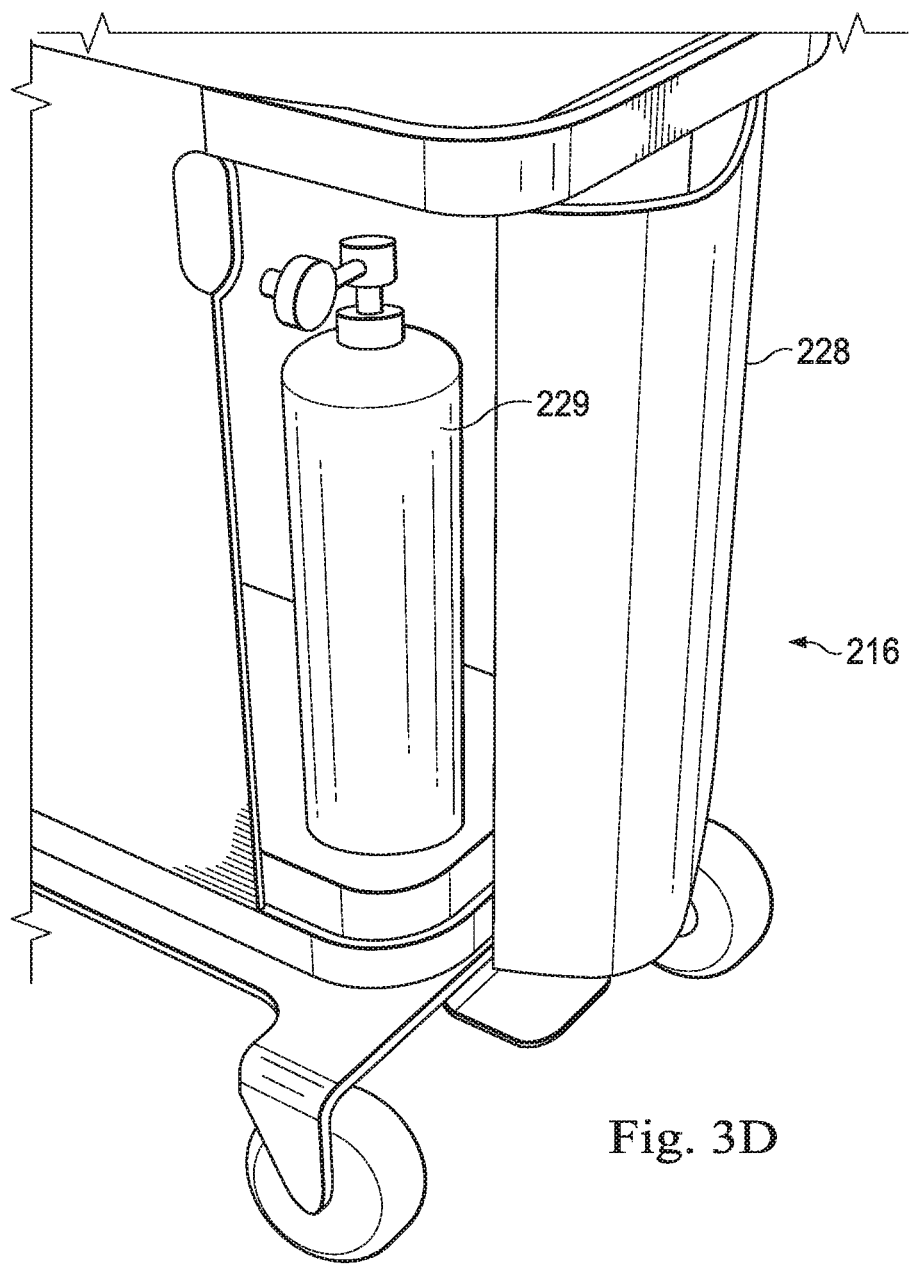

FIGS. 3A-D illustrate various portions of the cart 216, which may support the manipulator assembly 210 and the monitors 212 and may carry various components including processors (e.g. of the control system 112), vacuum equipment, air canisters, cables, etc. for performing various procedures on the patient P. As shown in FIG. 3B, the cart 216 may be mounted on a set of wheels 222 such that the cart 216 can be positioned at a desired location relative to the operating table T and the patient P. The wheels 222 can be positioned to protrude from the footprint of a cart body 224 to provide for stability of the system. Referring to FIG. 3A, a handle 220 can be provided at an upper portion of the cart 216 to allow for easy manipulation, and the wheels 222 may include brakes to lock the position of the cart 16 once it is placed at the desired location. In some embodiments, the handle 220 may be located at the front of the cart 216, making the handle 20 readily accessible during a medical procedure. In other embodiments, the handle 220 may be located at the back or sides of the cart 216. The cart 216 can include one or more doors 226 which can swing open to provide access to internal components 227 including computers. Such access may be needed for occasional maintenance. In some examples, two doors would provide for access from either or both sides of the cart 216 as illustrated in FIG. 3C. In some examples, as shown in FIG. 3D, a third door 228 can provide access to a gas canister 229 used to provide air for use with instrument cleaning. The gas canister 229 may be replaced by the hospital, surgeon, clinician, operator O, or any other person on a periodic basis. In some embodiments, the gas canister 229 may be placed in a front portion of the cart 216. This may be done to place the gas canister 229 closer to a probe instrument used for lens cleaning, thereby minimizing the amount of tubing needed for the gas canister 229.

FIGS. 4A-B illustrate an example of a plurality of monitors 212 for display of information used during various procedures on the patient P as described in regards to display system 110. In some embodiments, different types of information are displayed on different monitors 212. For example, a top monitor 230 can be used to provide navigational information such as the virtual navigational image including a path to a target and virtual image of the medical instrument. The virtual navigational image could include an anatomical model with the virtual image of the medical instrument superimposed based on a real sensed position of the medical instrument. A bottom monitor 232 can be used to provide driving views, for example virtual and/or real endoscopic camera views as seen from the distal end of the medical instrument. In some examples, the bottom monitor 232 can be used as a main screen and positioned so it is most visible to the clinician such that warnings would be displayed on the bottom monitor 232.

In some examples the top monitor 230 and the bottom monitor 232 are each mounted such that they can be adjusted in the vertical direction, horizontal direction, rotated about a vertical axis, and/or rotated about a horizontal axis to position either monitor at the desired viewing angle from the operator's point of view. A handle 234 can be used to adjust the position of the monitors 212. The handle 234 may be designed to allow a person, including operator O, to move the monitors 212 with either hand. In some embodiments, the handle 234 may be designed in a similar manner as the handle 220 on the cart 216.

The monitors 212 can be rotated such that they can fold for a compact stowed configuration as shown in FIG. 4B. This compact stowed configuration can help minimize the chance of damage to the monitors 212 as the monitors are moved through doorways, cramped spaces, busy passageways, and/or other similar locations.

FIGS. 5A-C illustrate the master control 218, which can include a master control console (MCC) 240 which may be mounted to a master control stand 242. The MCC 240 may include various input devices for controlling components of the manipulator assembly 210. For example U.S. patent application Ser. No. 62/357,272 filed Jun. 30, 2016, titled "SYSTEMS AND METHODS OF STEERABLE ELONGATE DEVICE" which is hereby incorporated by reference in its entirety, discloses examples of various MCCs including such input devices. The MCC 240 can be mounted to the master control stand 242 in a manner which provides for height, pitch, and/or yaw adjustments. In some examples, the MCC 240 can include a surface supporting wrists of a surgeon or clinician or operator O at an ergonomic angle. In some embodiments, the yaw of the MCC 240 is adjusted to an angle for ideal ergonomics. In some embodiments, this may be done using dual clutches located underneath the MCC 240. The master control stand 242 may be mounted on a plurality of wheels 244 allowing the MCC 240 to be positioned at a desired location relative to the operating table T, within the operating room, or outside the operating room. In some embodiments, the surgeon, clinician, or operator O can maintain a line of sight to the monitors 212 when operating the master control 218. Additionally, in some embodiments, the surgeon, clinician, or operator O may move the master control 218 while needing to reach the manipulator assembly 210 and the patient P.

As shown in FIG. 5B, a base plate 246 may be fixed to a bottom portion of the master control stand 242 to provide stability or to provide support for various instruments such as a fluoroscope foot pedal. For example, when fluoroscopy is to be used during a procedure, it can be convenient to utilize a foot pedal to activate and deactivate fluoroscopy to allow a surgeon, clinician, or operator O to continue manipulating the medical instruments without disruption. The surgeon, clinician, or operator O may be able to move the master control 218 and the foot pedal in tandem. The foot pedal may rest on the base plate 246 providing such that it may be easily moved with the MCC 240 to the desired location in the operating room.

FIGS. 6A and 6B are simplified diagrams of side views of a patient coordinate space including a medical instrument mounted on an insertion assembly according to some embodiments. In some embodiments, the patient coordinate space may include a medical instrument system. In some embodiments, the medical instrument system may be used as medical instrument 104 in an image-guided medical procedure performed with teleoperated medical system 100. In some examples, the medical instrument system may be used for non-teleoperational exploratory procedures or in procedures involving traditional manually operated medical instruments, such as endoscopy. Optionally, the medical instrument system may be used to gather (i.e., measure) a set of data points corresponding to locations within anatomic passageways of a patient, such as patient P.

The medical instrument system includes an elongate device, such as a flexible catheter, coupled to a drive unit. The elongate device includes a flexible body having a proximal end and a distal end or tip portion. In some embodiments, the flexible body has an approximately 3 mm outer diameter. Other flexible body outer diameters may be larger or smaller.

The flexible body includes a channel sized and shaped to receive a medical instrument. The medical instrument can be extended from the flexible body according to some embodiments. In some embodiments, the medical instrument may be used for procedures such as surgery, biopsy, ablation, illumination, irrigation, or suction. The medical instrument can be deployed through the channel of the flexible body and used at a target location within the anatomy. The medical instrument may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, catheters, sensors, and/or the like. In various embodiments, the medical instrument is a biopsy instrument, which may be used to remove sample tissue or a sampling of cells from a target anatomic location. The medical instrument may be used with an image capture probe also within the flexible body. In various embodiments, the medical instrument may be an image capture probe that includes a distal portion with a stereoscopic or monoscopic camera at or near the distal end of the flexible body for capturing images (including video images) that are processed by a visualization system for display and/or provided to a tracking system to support tracking of the distal end and/or one or more of the segments. The image capture probe may include a cable coupled to the camera for transmitting the captured image data. In some examples, the image capture instrument may be a fiber-optic bundle, such as a fiberscope, that couples to the visualization system. The image capture instrument may be single or multi-spectral, for example capturing image data in one or more of the visible, infrared, and/or ultraviolet spectrums. Alternatively, the medical instrument may itself be the image capture probe. The medical instrument may be advanced from the opening of the channel to perform the procedure and then retracted back into the channel when the procedure is complete. The medical instrument may be removed from the proximal end of the flexible body or from another optional instrument port along the flexible body.

In some embodiments, the medical instrument system may include a flexible bronchial instrument, such as a bronchoscope or bronchial catheter, for use in examination, diagnosis, biopsy, or treatment of a lung. The medical instrument system is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

In some examples, the medical instrument system may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

As further shown in FIGS. 6A and 6B, a surgical environment 300 includes a patient P positioned on the table T of FIG. 1. Patient P may be stationary within the surgical environment in the sense that gross patient movement is limited by sedation, restraint, and/or other means. Cyclic anatomic motion including respiration and cardiac motion of patient P may continue, unless patient P is asked to hold his or her breath to temporarily suspend respiratory motion. Accordingly, in some embodiments, data may be gathered at a specific phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a manipulator assembly (e.g., manipulator assembly 102, 210) that couples to point gathering instrument 304 to control insertion motion (i.e., motion along the A axis) and, optionally, motion of a distal end 318 of a medical instrument 310 (or other type of elongate device) in multiple directions including yaw, pitch, and roll. Instrument carriage 306 or insertion stage 308 may include actuators, such as servomotors, (not shown) that control motion of instrument carriage 306 along insertion stage 308. In some embodiments, instrument carriage 306 together with insertion stage 308 may also be referred to as a flexible instrument manipulator (FIM).

Further, medical instrument 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of medical instrument 310. Point gathering instrument 304 may be substantially similar to the medical instrument system discussed above.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 6A shows instrument body 312 and instrument carriage 306 in a retracted position along insertion stage 308. In this retracted position, proximal point 316 is at a position $L_0$ on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of medical instrument 310 may be positioned just inside an entry orifice of patient P. Also in this position, position measuring device 320 may be set to a zero and/or another reference value (e.g., I=0). In FIG. 6B, instrument body 312 and instrument carriage 306 have advanced along the linear track of insertion stage 308, and distal end 318 of medical instrument 310 has advanced into patient P. In this advanced position, the proximal point 316 is at a position $L_1$ on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position $L_x$ of proximal point 316 relative to position $L_0$. In some examples, position $L_x$ may further be used as an indicator of the distance or insertion depth to which distal end 318 of medical instrument 310 is inserted into the passageways of the anatomy of patient P.

FIG. 7 illustrates the medical instrument 310 positioned within an anatomic passageway of a patient anatomy. In this embodiment, the anatomic passageway is an airway of a human lung 350. In alternative embodiments, the medical instrument 310 may be used in other passageways of an anatomy.

In accordance with embodiments described below, it may be advantageous to provide a manipulator assembly 102 that is capable of maintaining a desired orientation of the medical instrument while also enabling vertical and rotational adjustment. The present disclosure proposes the below mechanisms to provide for the vertical and rotational adjustment while maintaining a desired orientation of the medical instrument.

Referring again to FIG. 2, the manipulator assembly 210 includes a support structure 420 moveably mounted to the cart 216. In alternative embodiments, the manipulator assembly 210 may be mounted to a separate structure such as an operating table, cabinet, counter, or an additional cart. At one end (e.g., a proximal end), the support structure 420 may be mounted to the cart 16 via a shoulder 415 of a base joint 410, and at the other end (e.g., a distal end), the support structure 420 may be coupled to a distal support 450. The distal support 450 may carry, support, and/or be coupled to various types of components including trays, manipulator assemblies, instruments, or any other similar component. More specifically, the distal support 450 may be coupled to an instrument manipulator 417 such as a flexible instrument manipulator (FIM) that may include the instrument carriage 306 and the insertion stage 308 to which the instrument body 312, and therefore the medical instrument 310, is coupled. As described in greater detail below, the support structure 420 may rotate in pitch and yaw motions about axes associated with the base joint 410 to allow for instrument adjustment. In addition, the support structure 420 may include a telescoping arm that allows for translational adjustment in both extension and retraction. Thus, as the support structure 420 is rotated relative to the cart 16 about the base joint 410, the telescoping support structure 420 allows translational adjustment of the distal support 450 which can be coupled to or supporting equipment such as medical instrument 310 to consistently maintain an orientation of the medical instrument 310 to a fixed reference (for example, the ground).

The base joint 410 may be rotatably connected to a flat top surface of the cart 16 to allow the base joint 410 to rotate about a vertical axis V1. The shoulder 415 of the base joint 410 may be coupled to the support structure 420. The support structure 420 includes a proximal link 430 and a telescoping arm or distal link 440. The shoulder 415 of the base joint 410 may be pivotally coupled to the proximal link 430 of the support structure 420, allowing the proximal link 430 of the support structure 420 to rotate in a pitch motion 510 about a horizontal axis H1 of the base joint 410. The proximal link 430 may rotate 180 degrees or beyond 180 degrees about the horizontal axis H1.

The distal end of the distal link 440 may be coupled to the distal support 450 such that a desired predetermined orientation of the distal support is maintained. The distal support 450 may be connected to the insertion stage 308 through a rotational joint 460, which allows the insertion stage 308 to rotate relative to the distal support 450. The support structure 420 allows a desired orientation of the distal support 450 to be maintained relative to a fixed reference such as the ground, even as the support structure 420 is rotated about the axes V1, H1. This allows the coupled medical instrument 310, to be maintained at a desired orientation. In various embodiments, the desired orientation of the medical instrument 310 may be relative to a predetermined orientation of the distal support 450.

FIGS. 8A-C show the support structure 420 positioned in exemplary configurations according to embodiments of the present disclosure. In FIG. 8A, the support structure 420 is shown in a folded and stowed configuration. In FIG. 8B, the support structure 420 is shown in an unfolded configuration with the distal link 440 retracted within a channel of the proximal link 430. In FIG. 8C, the support structure 420 is shown in an unfolded configuration with the distal link 440 extended from the channel of the proximal link 430.

As seen from FIGS. 8A-C, the support structure 420 including the proximal link 430 and the connected distal link 440, may rotate in the pitch motion 510 about the horizontal axis H1 of the base joint 410 (see FIG. 2). In various embodiments, the support structure 420 including the proximal link 430 and the distal link 440, may rotate 180 degrees or beyond 180 degrees. The distal link 440 may be extended out from a channel of the proximal link 430, as shown in FIG. 8C. In various embodiments, the proximal link 430 and the connected distal link 440 may rotate in the yaw motion 520 about the vertical axis V1 of the base joint 410 in a 360 degree range. The base joint 410 and/or the proximal link 430 may include brakes to restrict motion about the axes H1, V1. In some embodiments, brakes may be engaged or released manually by depressing a button or switch, allowing the support structure 420 to be manually positioned and locked. In various embodiments, the proximal link 430 and the distal link 440 may be positioned using electronic circuitry and controls, including motors to avoid manual intervention. In some examples, a motor positioned within the base joint 410 or within the cart 16 can be used to direct drive or drive the rotation of the support structure 420 using any combination of gears, pulleys, and/or belts to position the support structure 420. In some embodiments, the support structure 420 may be designed for easy stowing of the teleoperational manipulator assembly 400. In various embodiments, the teleoperational manipulator assembly 400 can, in one motion, be stowed so that the FIM 417 sits on top of the cart 16.

As shown in FIGS. 8A-C, a consistent orientation of the distal support 450 may be maintained with all configurations of the support structure 420. For instance, in FIGS. 8A-C, the orientation of the distal support 450 is maintained parallel to ground in all configurations of the support structure 420. When positioning the FIM 417 during the medical procedure, the support structure 420 allows the distal support, and therefore the FIM 417 and the medical instrument 310, to remain in the desired predetermined orientation, regardless of the vertical, horizontal, and rotational adjustments of the support structure 420.

FIGS. 9A-D illustrate, inter alia, a linkage mechanism 600, e.g. a parallel linkage mechanism that allows maintenance of the desired orientation of the distal support 450 during rotation and extension of the support structure 420. In this embodiment, the parallel linkage mechanism 600 includes an input gear 610 (which may also be an input bevel gear), an output gear 630 (which may also be an output bevel gear), an input pinion 620 (which may also be an input pinion gear), an output pinion 640 (which may also be an output pinion gear), and an extension mechanism 650 which mechanically maintains the desired predetermined orientation (e.g., parallel to the ground) of the distal support 450 during vertical, horizontal, or rotational adjustment of the support structure 420 (which may include the proximal link 430 and the distal link 440). As an operator O adjusts the proximal link 430 (and/or the distal link 440) to raise or lower the distal support 450, the distal support 450 remains in its desired predetermined orientation. In some embodiments, a brake (not shown), such as a magnetic brake, may be provided which locks telescoping motion of the distal link 440 relative to the proximal link 430 when the support structure 420 is positioned at a desired location. The brake could be fixed to the distal link 440 and when activated would prevent telescoping movement by locking to a magnetic strip (not shown) fixedly positioned within the proximal link 430.

FIGS. 9A and 9B show exemplary embodiments of the support structure 420 according to the present disclosure. FIG. 9A shows an exemplary embodiment of the support structure 420 with the distal link 440 retracted within a channel 435 of the proximal link 430. In some embodiments, the distal link 440 may be coupled to the proximal link 430 using a plurality of linear bearings on slide rails. The proximal link 430 may include an input bevel gear 610 and an input pinion 620. The distal link 440 may include an output bevel gear 630 and an output pinion 640. The input pinion 620 may be connected to the output pinion 640 via an extension mechanism 650 including a spline 652 (which may also be a sliding spline) and a tubular member 654 (which may also be an inner tube). The tubular member 654 may extend at least partially over the spline 652 while allowing the spline 652 to linearly retract within and extend from the tubular member 654. As shown, the toothed gear face of the input bevel gear 610 faces the opposite direction of the toothed gear face of the output bevel gear 630 and the gears 610, 630 are positioned on opposite sides of the extension mechanism 650. FIG. 9B shows an exemplary embodiment of the support structure 420 with the distal link 440 extended from the channel 435 of the proximal link 430. In the exemplary embodiment shown in FIG. 9B, the support structure 420 is shown with the spline 652 extended from the tubular member 654.

The extension mechanism 650 is also configured to rotate about a longitudinal axis L1 (see FIG. 11) passing longitudinally through the spline 652 and the tubular member 654. The input bevel gear 610 may be fixedly connected to the shoulder 415 of the base joint 410. The input bevel gear 610 may be rotationally stationary about horizontal axis H1, and may serve as a reference for rolling motion of the input pinion 620. As the proximal link 430 (and the distal link 440) rotates in the pitch motion 510 about the horizontal axis H1, the input pinion 620 rolls along the input bevel gear 610 (orbiting the axis H1) in a connected arrangement, and the extension mechanism 650 rotates about its longitudinal axis L1. To facilitate the motion between the input bevel gear 610 and the input pinion 620, the input bevel gear 610 and the input pinion 620 may include cogs or teeth with equal pitches.

The output bevel gear 630 may be fixedly connected to the distal support 450. The fixed connection may be achieved with screws 635 to fixedly connect the output bevel gear 630 to the distal support 450, but other fastening mechanisms or an integral connection of the output bevel gear 630 and distal support 450 may also be suitable. The output bevel gear 630 is rotationally stationary about its own horizontal axis H2 and may rotate (i.e., orbit) about the horizontal axis H1 and around the input bevel gear 610 as the support structure 420 moves upwards or downwards in the pitch motion 510. The output bevel gear 630 may also serve as a reference for rolling motion of the output pinion 640. In other words, as the proximal link 430 (and the distal link 440) rotates in the pitch motion 510 about the horizontal axis H1 of the base joint 410, the extension mechanism 650 rotates about its longitudinal axis L1 and the output pinion 640 rolls along the output bevel gear 630. To facilitate the motion between the output bevel gear 630 and the output pinion 640, the output bevel gear 630 and the output pinion 640 may include cogs or teeth with equal pitches.

FIGS. 9C and 9D show exemplary embodiments of movement of the support structure 420 in the pitch motion 510 about the horizontal axis H1. FIG. 9C shows an exemplary embodiment with the support structure 420 angled upward. FIG. 9D shows an exemplary embodiment with the support structure 420 angled downward. In each of the embodiments shown in FIGS. 9A-D, an orientation of the distal support 450 is consistently maintained. As shown in FIGS. 9A-D, a horizontal surface 451 of the distal support 450 remains parallel to a top surface of the cart 16 or parallel to the ground through all of the pitch orientations of the support structure 420. This allows the coupled instrument body 312, and therefore the medical instrument 310, to be maintained at a desired or predetermined orientation.

In various embodiments, the pitches of teeth of the input bevel gear 610 may substantially be the same as or different from the pitches of teeth of the output bevel gear 630. Similarly, the pitches of teeth of the input pinion 620 may substantially be the same as or different from the pitches of teeth of the output pinion 640. In various embodiments, the sizes of the input bevel gear 610 and the output bevel gear 630 may substantially be the same or different with respect to each other, and the sizes of the input pinion 620 and the output pinion 640 may substantially be the same or different with respect to each other.

FIG. 10 shows an exemplary configuration of the input and output bevel gears 610, 630 and the input and output pinions 620, 640 according to an embodiment of the present disclosure. In this configuration, the sizes of the input bevel gear 610 and the output bevel gear 630 are substantially the same, and the sizes of the input pinion 620 and the output pinion 640 are substantially the same. Also, the pitches of the teeth of the input bevel gear 610, the output bevel gear 630, the input pinion 620, and the output pinion 640 are substantially the same to facilitate the rolling motions of the pinions on the bevel gears. Due to the similarity in the sizes and the pitches of the bevel gears and the pinions, the pinions may roll along the respective bevel gears at the same rate. As seen in FIG. 10, the input bevel gear 610 and the output bevel gear 630 may be disposed on opposite sides of the extension mechanism 650, and the output pinion 640 may be connected to the input pinion 620 by the extension mechanism 650.

In this exemplary configuration, as the proximal link 430 and the distal link 440 are rotated upwards (see FIG. 9C), the extension mechanism 650 rotates about its longitudinal axis L1, as shown by arrow 750. When the input bevel gear 610 is rotationally stationary about its horizontal axis H1 and the output bevel gear 630 is rotationally stationary about its horizontal axis H2 but rotational (e.g., orbital) about the horizontal axis H1, the input pinion 620 rolls along the input bevel gear 610 in the direction shown by arrow 720 while the output pinion 640 rolls along the output bevel gear 630 in the direction shown by arrow 730. The input pinion 620 rolls along the input bevel gear 610 at the same rate at which the output pinion 640 rolls along the output bevel gear 630. Similarly, as the proximal link 430 and the distal link 440 are angled downwards (see FIG. 9D), the extension mechanism 650 rotates about its longitudinal axis L1, as shown by arrow 710. The input pinion 620 rolls along the input bevel gear 610 in the direction shown by arrow 760 while the output pinion 640 rolls along the output bevel gear 630 in the direction shown by arrow 770. Again, the input pinion 620 rolls along the input bevel gear 610 at the same rate at which the output pinion 640 rolls along the output bevel gear 630.

Regardless of whether the support structure 420 (which may include the proximal link 430 and the distal link 440) is adjusted upwards or downwards, and regardless of the directions in which the input and output pinions 620, 640 roll over the input and output bevel gears 610, 630, respectively, the orientation of the output bevel gear 630 is maintained because the output bevel gear 630 is rotationally stationary with respect to its own horizontal axis H2. In other words, regardless of whether the output bevel gear 630 moves upwards or downwards (in a circular path) with respect to the input bevel gear 610, the orientation of the output bevel gear 630 is maintained. Because the output bevel gear 630 is fixedly connected to the distal support 450, the orientation of the distal support 450 is also maintained regardless of the vertical, horizontal, or rotational adjustment of the support structure 420.

The above arrangement of the bevel gears 610, 630, pinions 620, 640, and extension mechanism 650 serves as a parallel linkage mechanism (e.g., parallel linkage mechanism 600) which mechanically maintains the desired predetermined orientation (e.g., parallel to the ground) of the distal support 450 during vertical, horizontal, or rotational adjustment of the support structure 420. As an operator O adjusts the proximal link 430 (and/or the distal link 440) to raise or lower the distal support 450, the distal support 450 remains in its desired predetermined orientation.

The parallel linkage mechanism 600 is effective in maintaining parallelism even as the extension mechanism 650 enables the distal link 440 to extend from and retract within the channel 435 of the proximal link 430. As shown in FIG. 11, the spline 652 extends into and is movable within a passage 655 in tubular member 654 to allow the length of the extension mechanism 650 to vary (e.g., retract or extend). In various embodiments, the spline 652 may be tubular or may be a solid rod. In various embodiments, the tubular member 654 may be tubular along only a partial length or tubular along an entire length. In various embodiments, the spline 652 is axially coupled to the tubular member 654 by a stop mechanism (not shown) such that the spline 652 may linearly move to extend from and retract within the passage 655 without disconnecting from the tubular member 654. In various embodiments, the spline 652 may be provided with grooves 830 along its length, and the tubular member 654 may include protrusions, including for example bearings, that mate with and move within the grooves to enable linear movement of the spline 652 during the retraction and extension. The use of bearings may provide a substantially frictionless interface between the spline and the tubular member 654. The grooves 830 and the mated protrusions may also prevent the spline 652 from rotating relative to the tubular member 654. As the spline 652 linearly moves to retract within the tubular member 654, the distal link 440 retracts within the channel 435 of the proximal link 430 (see FIG. 9A). Similarly, as the spline 652 linearly moves to extend out from the tubular member 654, the distal link 440 extends from the channel 435 of the proximal link 430 (see FIG. 9B). In various embodiments, the grooves may be in the tubular member, and the projections, including any bearings, may extend from the spline.

The rotational motion of the spline 652 is coupled to the rotational motion of the tubular member 654 such that the spline 652 and the tubular member 654 rotate about the longitudinal axis L1 at the same rate. As a result, the input pinion 620 connected to the tubular member 654 rotates at the same rate as the output pinion 640 connected to the spline 652. For instance, with respect to FIG. 10, the spline 652 and the tubular member 654 rotate in the direction shown by arrow 750 when the support structure 420 is adjusted upwards (see FIG. 9C). Also, the spline 652 and the tubular member 654 rotate in the direction shown by arrow 710 when the support structure 420 is adjusted downwards (see FIG. 9D). In this way, this exemplary configuration of the extension mechanism 650 enables the orientation of the above discussed parallel linkage mechanism 600 and the above discussed distal support 450 to be maintained during the linear and vertical movements of the support structure 420.

FIG. 15 shows another exemplary linkage mechanism 1200, e.g., a parallel linkage mechanism that uses hydraulic push-pull cylinders, according to an embodiment of the present disclosure. The parallel linkage mechanism 1200 includes two cylinders 1210, 1230 including respective pistons 1220, 1240. In place of the input and output bevel gears, the present embodiment may include input and output disks. Similar to the input bevel gear 610 (see FIG. 9A), an input disk 1216 may be rotationally stationary about its own horizontal axis H1. Similar to the output bevel gear 630 (see FIG. 9A), the output disk 1218 may be rotationally stationary about its own horizontal axis H2, but may rotate orbitally about horizontal axis H1. A distal support 1252 may be fixedly connected to the output disk 1218 similar to the way the distal support 450 (see FIG. 9A) is fixedly connected to the output bevel gear 630 (see FIG. 9A). In various embodiments, similar to the embodiment shown in FIG. 10, the input and output disks 1216, 1218 may be disposed on opposite sides of the cylinders 1210, 1230.

Cylinder 1210 may be connected to the output disk 1218 in a distal link 1254 via a distal hinged connection 1250, and the corresponding piston 1220 may be connected to the input disk 1216 in a proximal link 1256 via a hinged connection 1270. A shoulder 1258 may be pivotally coupled to the proximal link 1256, allowing the proximal link 1256 to rotate in a pitch motion 1259 about a horizontal axis H1. Cylinder 1230 may be connected to the input disk 1216 in the proximal link 1256 via a hinged connection 1280, and the corresponding piston 1240 may be connected to the output disk 1218 in the distal link 1254 via a hinged connection 1260. As discussed below, when the distal link 1254 extends and retracts within the proximal link 1256, the cylinders 1210, 1230 remain parallel to each other throughout the movements, and the distance between the input and output disks 1216, 1218 changes according to the motion of the distal link 1254. For example, in one exemplary embodiment, if the support structure rotates counter-clockwise about the horizontal axis H1, the piston 1220 would retract into the cylinder 1210. At the same time, during the rotation of the support structure counter-clockwise about the horizontal axis H1, the piston 1240 would extend out from the cylinder 1230. In addition to the extension and retraction, when the parallel linkage mechanism 1200 rotates in the pitch motion 510 (see FIGS. 8A-C) about the horizontal axis H1, the hinged connections 1250, 1260, 1270, 1280 flex to maintain the desired orientation of distal support 1252 connected to the output disk 1218.

The cylinder 1210 may include chambers 1212, 1214 housing an incompressible fluid. Similarly, the cylinder 1230 may include chambers 1232, 1234 also having the same or a different incompressible fluid. Chamber 1212 may be cross-connected with chamber 1234 via a cross-connection tube 1292, and chamber 1214 may be cross-connected with chamber 1232 via a cross-connection tube 1290, as shown in FIG. 15, to enable the push-pull configuration.

When the distal link 1254 extends from the proximal link 1256, piston 1220 extends out from the cylinder 1210, thereby increasing the volume in chamber 1212 and decreasing the volume in chamber 1214. At the same time, piston 1240 also extends out from cylinder 1230, thereby increasing the volume in chamber 1232 and decreasing the volume in chamber 1234. During the extension, the incompressible fluid in chamber 1214 is transferred into chamber 1232 via the cross-connection tube 1290, and the incompressible fluid in chamber 1234 is transferred into chamber 1212 via the cross-connection tube 1292. In this way, the cylinders 1210, 1230 in the push-pull configuration maintain equal lengths and maintain the orientation of input disk 1216 with respect to output disk 1218. In addition, when the support structure (which may be similar to the support structure 420 in FIG. 9A) rotates in the pitch motion 510 (see FIGS. 8A-C) about the horizontal axis H1, the hinged connections 1250, 1260, 1270, 1280 flex to maintain the orientation of the output disk 1218 (which is rotationally stationary about its own horizontal axis H2). For example, in one exemplary embodiment, if the support structure rotates counter-clockwise about the horizontal axis H1, the piston 1220 would retract into the cylinder 1210. At the same time, during the rotation of the support structure, the piston 1240 would extend out from the cylinder 1230. In this way, the hinged connections 1250, 1260, 1270, 1280 and/or the cylinders 1210, 1230 allow the desired predetermined orientation of the distal support 1252 (which is fixedly connected to the output disk 1218) to be maintained.

When the distal link 1254 retracts within the proximal link 1256, piston 1220 also retracts in the cylinder 1210, thereby decreasing the volume in chamber 1212 and increasing the volume in chamber 1214. At the same time, piston 1240 retracts in cylinder 1230, thereby decreasing the volume in chamber 1232 and increasing the volume in chamber 1234. During the retraction, the incompressible fluid in chamber 1212 is transferred into chamber 1234 via the cross-connection tube 1292, and the incompressible fluid in chamber 1232 is transferred to chamber 1214 via the cross-connection tube 1290. In this way, the cylinders 1210, 1230 with pistons 1220, 1240 in the push-pull configuration maintain the distance between the hinged connections 1250, 1270 equal to the distance between hinged connections 1260, 1280 of the input disk 1216 and the output disk 1218. In addition, when the support structure (which may be similar to the support structure 420 in FIG. 9A) rotates in the pitch motion 510 (see FIGS. 8A-C) about the horizontal axis H1, the hinged connections 1250, 1260, 1270, 1280 flex to maintain the desired orientation of the output disk 1218 (which is rotationally stationary about its own horizontal axis H2). In this way, the hinged connections 1250, 1260, 1270, 1280 allow the desired predetermined orientation of the distal support 1252 (which is fixedly connected to the output disk 1218) to be maintained.

The above parallel linkage mechanism 1200, including the hydraulic cylinders 1210, 1230 in the push-pull configuration, allow the extension and retraction movement of the distal link 1254 while maintaining the orientation of the distal support 1252, and, therefore, the desired predetermined orientation of the medical instrument 310 (see FIGS. 6A-B).

FIG. 16 shows another exemplary linkage mechanism 1300, e.g., a parallel linkage mechanism including a ball-screw arrangement, according to an embodiment of the present disclosure. The parallel linkage mechanism 1300 may include two ball-screw drives 1310, 1340. The ball-screw drive 1310 may include a ball-screw 1330 assembled with an extended ball nut 1320, and the ball-screw drive 1340 may include a ball-screw 1360 assembled with an extended ball nut 1350. These ball-screw assemblies are configured to convert linear motion of the ball-screws drives 1310, 1340 into rotary motion, and vice versa. For instance, linear motion of the ball-screws 1330, 1360 in and out of the extended ball nuts 1320, 1350, may cause the extended ball nuts 1320, 1350 to rotate in a rotary motion. Similarly, rotary motion of the extended ball nuts 1320, 1350 about their respective longitudinal axes may cause in and out linear motion of the ball-screws 1330, 1360. The interfaces between the ball-screws 1330, 1360 and the extended ball nuts 1320, 1350 may include ball bearings (this is what a ball screw is rather than an extra feature added to something that is already a ball screw), which allow low friction movement within the ball-screw drives 1310, 1340.

The extended ball nuts 1320, 1350 may be connected to each other via a flexible shaft 1370 to couple the rotary motion of the extended ball nuts 1320, 1350 with respect to each other. For instance, the flexible shaft 1370 may enable the extended ball nuts 1320, 1350 to rotate at the same rate with respect to each other. In various embodiments, a pitch direction associated with the extended ball nut 1320 may be reversed with respect to a pitch direction associated with the extended ball nut 1350. This would enable the extended ball nut 1320 to rotate in the opposite direction with respect to the direction of rotation of the extended ball nut 1350.

As shown in FIG. 16, each of the ball-screw drives 1310, 1340 may be connected to the input disk 1322 (which in various embodiments may be an input bevel gear, which may be similar to input bevel gear 610 in FIG. 9A) and to the output disk 1324 (which in various embodiments may be an output bevel gear, which may be similar to output bevel gear 630 in FIG. 9A) to form the parallel linkage mechanism 1300. In various embodiments, the extended ball nut 1320 of the ball-screw drive 1310 may be connected to the input disk 1322 at joint 1380 by using one end of a joint plate 1390, and the extended ball nut 1350 of the ball-screw drive 1340 may be connected to the input disk 1322 at joint 1382 by using another end of the joint plate 1390. Similarly, the ball-screw 1330 of the ball-screw drive 1310 may be connected to the output disk 1324 at joint 1384 by using one end of a joint plate 1392, and the ball-screw 1360 of the ball-screw drive 1340 may be connected to the output disk 1324 at joint 1386 by using another end of the joint plate 1392.

As the distal link 1354 (which may be similar to distal link 440 in FIG. 9A) extends from or retracts within the channel 1362 (which may be similar to channel 435 in FIG. 9A) of the proximal link 1356 (which may be similar to proximal link 430 in FIG. 9A), the ball-screws 1330, 1360 linearly move out from or move within the extended ball nuts 1320, 1350, respectively. This linear motion is converted into rotary motion of the extended ball nuts 1320, 1350 about their respective longitudinal axes by the flexible shaft 1370.

For instance, the flexible shaft 1370 enables the extended ball nut 1320 to rotate at the same rate as the extended ball nut 1350. Also, the reverse pitch directions enable the extended ball nuts 1320, 1350 to rotate in opposite directions with respect to each other. Because of the equal linear motion of the ball-screws 1330, 1360 and the equal rotary motion of the extended ball nuts 1320, 1350, the ball-screw drives 1310, 1340 are effectively constrained to remain at the same length throughout the extension or retraction motion of the distal link 1354, thus maintaining the parallel linkage.

In various embodiments, the joints 1380, 1382 connecting the extended ball nuts 1320, 1350 to the input disk 1322, and the joints 1384, 1386 connecting the ball-screws 1330, 1360 to the output disk 1324 may include hinged joints. When the support structure (which may be similar to support structure 420 in FIG. 9A) is moved upward or downward to rotate in the pitch motion 510 (see FIGS. 8A-C) about the horizontal axis H1, the hinged joints flex to maintain the desired orientation of the output disk 1324, and therefore the fixedly connected distal support 1352 maintains a similar desired orientation. In this way, the parallel linkage mechanism 1300 maintains the parallelism between the ball-screw drives 1310, 1340 during the above rotational and extension/retraction motions of the support structure.

FIG. 17 shows another exemplary linkage mechanism 1500, e.g., a parallel linkage mechanism including a chain and pulley configuration, according to an embodiment of the present disclosure. The parallel linkage mechanism 1500 may include a chain 1510. In some embodiments, the chain 1510 may be metal (e.g., a metal with high stiffness). In other embodiments, the chain 1510 may be made of any other flexible but generally inelastic material. The chain 1510 may be coupled to an outer edge of four pulleys 1540, 1550, 1560, 1570 in the configuration shown in FIG. 17. The chain 1510 may also be coupled to an outer edge of an input pulley 1520 and an outer edge of an output pulley 1530 in the configuration shown in FIG. 17. In various embodiments, the chain 1510 may be coupled to the pulleys 1540, 1550, 1560, 1570, the input pulley 1520, and the output pulley 1530 in a double-wrapped manner so as to provide, for example, additional stiffness of the chain 1510. Similar to the input bevel gear 610 (see FIG. 9A), the input pulley 1520 may be rotationally stationary about its own horizontal axis H1. Similar to the output bevel gear 630 (see FIG. 9A), the output pulley 1530 may be rotationally stationary about its own horizontal axis H2, but may rotate orbitally about horizontal axis H1. A distal support 1552 may be fixedly connected to the output pulley 1530 similar to the way the distal support 450 (see FIG. 9A) is fixedly connected to the output bevel gear 630 (see FIG. 9A).

As shown in FIG. 17, the input pulley 1520 is coupled to a proximal link 1556. In an exemplary embodiment, the output pulley 1530 is coupled to a distal link 1554. In various embodiments, the input pulley 1520 may be coupled to the proximal link 1556 at a shoulder 1558 of a base joint of a support structure (which may be similar to support structure 420 in FIG. 9A). Additionally, a distal end of the distal link 1554 may be fixedly coupled to the distal support 1552 (which may be similar to the distal support 450 in FIG. 9A). In an exemplary embodiment, as the parallel linkage mechanism 1500 rotates in the pitch motion 510 (see FIGS. 8A-C) about the horizontal axis H1, the chain 1510 provides a 1:1 rotation. As such, as the parallel linkage mechanism 1510 rotates in the pitch motion 510 about the horizontal axis H1, the input pulley 1520 rotates, and the output pulley 1530 rotates an equivalent degree of rotation. This equivalent rotation between the input pulley 1520 and the output pulley 1530 maintains a desired orientation of the distal instrument support 1552 (e.g., parallel to the ground).

As shown in FIG. 17, the pulleys 1560, 1570 may be fixedly coupled to a counterweight block 1580 (which may be similar to the counterweight block 920 in FIG. 12). In various embodiments, the counterweight block 1580 may move toward a pivot point C (see FIG. 12—the counterweight block 1580 and other aspects of a counterbalance arrangement will be further discussed with respect to FIGS. 12-14 below). As the counterweight block 1580 moves toward the pivot point C (see FIG. 12), the pulleys 1560, 1570 may move toward the pivot point C along with the counterweight block 1580 due to the fixed connection. As such, in an exemplary embodiment, the chain 1510 does not provide additional length even during the linear movement of the pulleys 1560, 1570 and the counterweight block 1580. This lack of additional length in the chain 1510 helps maintain a desired orientation of the distal instrument support 1552 (e.g., parallel to the ground).

Additionally, in some embodiments, as the distal link 1554 extends from or retracts within a channel 1562 of the proximal link 1556, a linear distance between input pulley 1520 and output pulley 1530 increases. Also, in an exemplary embodiment, as the distal link 1554 extends from or retracts within the channel 1562 of the proximal link 1556, the pulleys 1560, 1570 (which are fixedly connected to the counterweight block 1580) translate toward the input pulley 1520. The length of the chain 1510 between the pulleys 1560, 1570 and the pulleys 1540, 1550 decreases, which increases the length of the chain 1510 between the pulleys 1540, 1550 and the output pulley 1530. As such, the parallel linkage mechanism 1500 may, in some embodiments, extend or retract within the channel 1562 without causing rotation of the output pulley 1530 in the pitch motion 510 (see FIGS. 8A-C) relative to the input pulley 1520.

All parallel linkage mechanisms discussed above are compatible with and may be provided in combination with the below discussed mechanisms that enable provision of a counter balance.

The various mechanisms that enable provision of a counter balance to balance a change in center of mass associated with rotation of a telescoping support structure (e.g., support structure 420) will now be described. As discussed above, the support structure 420 (which may include the proximal link 430 and the distal link 440) may rotate in the pitch motion 510 about the horizontal axis H1, and in the yaw motion 520 about the vertical axis V1 (see FIGS. 8A-C). In addition, the distal link 440 of the support structure 420 may retract within and extend from the channel 435 of the proximal link 430. Because the distal support 450 is connected to the output bevel gear 630 of the distal link 440, the distal support 450 also moves as the distal link 440 rotates about the axes H1, V1, extends, and retracts. The rotation, extension, and/or retraction discussed above causes the center of mass of the telescoping support structure (e.g., support structure 420) to shift. Additionally, during the rotation, extension, and/or retraction discussed above, the distal support 450 may further imbalance the system because the distal support 450 is connected to the FIM 417, which, together with the support structure 420, can weigh, for example, about 20 kg.

In an exemplary embodiment, as the distal link 440 extends from the channel 435 of the proximal link 430, the distal support 450 connected to the FIM 417 also extends. During this extension, a lever arm supporting the weight of the FIM 417 increases, which may cause the lever arm to apply more force to the support structure 420. The highest force may be applied at the most distal portion of the FIM 417, and the amount of force may scalingly decrease in the direction from the distal support 450 to the base joint 410 (see FIGS. 8A-C) along the support structure 420 until reaching a pivot point of the support structure 420 (e.g., the pivot point C in FIG. 12). A counter balance that is slidable along the length of the support structure 420 may be needed to counteract the force applied by the lever arm.

A counterbalance mechanism may be provided to counter the imbalance created by the above movements of the support structure 420 and the FIM 417. The present disclosure contemplates providing spring-loading in the base joint 410 in combination with a counter block (discussed below), which moves along a length of the distal link 440 to counterbalance the movement of the FIM 417 and the support structure 420. In various embodiments, the base joint 410 may be spring-loaded either directly or via a lever arm connected to a cable and a spring housed within the cart 16.

FIG. 12 shows an exemplary counterbalance arrangement according to an embodiment of the present disclosure. A rotational center is located at a pivot point C of the base joint 410, through which horizontal axis H1 passes, may serve as the pivot point for the support structure 420 (which may include the proximal link 430 and the distal link 440). The system may be considered as being at equilibrium at the pivot point C when the distal link 440 is completely retracted within channel 435 of the proximal link 430, as shown in FIG. 12. This equilibrium may be lost, and the system may become increasingly imbalanced as the distal link 440 progressively extends out from the channel 435 of the proximal link 430 because the center of mass of the support structure 420 is shifted. To maintain equilibrium at pivot point C, the effects of gravity on the moving support structure 420 may be balanced, at least in part, by using a linear spring 910 at the base of the base joint 410. At equilibrium, the following equation is satisfied:

$$K=(M*g*L)/(a*b), \text{ where}$$

K may be the spring constant of the linear spring 910 that gives the rate of force per inch compression (e.g., 52 kg/inch); M may be a mass (e.g., 20 kg) of the support structure 420 plus the FIM 417 at the distal end of the distal link 440; g is the gravitational constant (g=9.8 m/s$^2$); L may be a distance between the pivot point C and the center of the output bevel gear 630, to which the FIM 417 is coupled; "b" may be a distance between the pivot point C and the linear spring 910; and "a" may be a distance between the linear spring 910 and an anchor point.

As the distal link 440 progressively extends out from channel 435 of the proximal link 430, the distance L varies (i.e., increases) while K remains constant. As a result, the above equation no longer remains satisfied and the equilibrium at the pivot point C is lost. To maintain the equilibrium, the effects of the variation in distance L should be addressed. The present disclosure provides a counterweight block 920 (which may also be a counterweight balance and/or a sliding counterweight mechanism) for this purpose. In various embodiments, a mass of the counterweight block 920 may be substantially equal to the mass of the FIM 417 plus the support structure 420. For example, a weight of the counterweight block 920 may be substantially the same as the weight of the FIM 417 plus the support structure 420.

At equilibrium, the counterweight block 920 may be placed proximal to the FIM 417 (which is connected to the distal support 450). As the distal link 440 progressively extends out from the channel 435 of the proximal link 430 and the distance L increases, a counterbalance mechanism is provided that shifts or moves the counterweight block 920 towards the pivot point C. This enables the effective mass (M) to remain the same as at equilibrium, thereby nullifying the effects of the increase in L. In various embodiments, the distance by which the counterweight block 920 is shifted is substantially equal to the distance by which L is increased. In other words, the distance by which the counterweight block 920 is shifted is substantially equal to the distance by which the distal link 440 extends from or retracts within channel 435 of the proximal link 430. Because the mass of the counterweight block 920 is substantially equal to the mass of the FIM 417 plus the support structure 420, and because the counterweight block 920 is moved by a distance equal to the increase in L, the effects of gravity on the movement of the FIM 417 and the support structure 420 are nullified, and equilibrium at the pivot point C is maintained.

The mechanisms that allow movement of the counterweight block 920 will now be described. FIG. 13A shows an exemplary configuration of the support structure 420 at equilibrium about the pivot point C, according to an embodiment of the present disclosure. As previously discussed, the support structure 420 may include the proximal link 430 and the distal link 440. Also, at its distal end, the distal link 440 may be fixedly connected to the distal support 450 that is coupled to the FIM 417. As shown in FIG. 13A, a belt 1010 (which may also be a counterweight belt) may be provided in a pulley structure with pulleys 1060, 1062, 1064, 1066 such that the belt 1010 may be divided into an upper portion 1012 and a lower portion 1014. In various embodiments, the pulleys 1060, 1062, 1064, 1066 may be mounted on or connected to the proximal link 430. A section of the upper portion 1012 of the belt 1010 may be fixedly coupled to the counterweight block 920 at link 1020 such that the counterweight block 920 moves linearly as the belt 1010 rotates around the pulleys 1060, 1062, 1064, 1066. In various embodiments, the counterweight block 920 linearly moves towards the pivot point C as the belt 1010 rotates clockwise, and the counterweight block 920 linearly moves towards the distal support 450 as the belt 1010 rotates counter-clockwise. A section of the lower portion 1014 of the belt 1010 may be fixedly connected to a telescoping block 1030 at link 1040 such that the belt 1010 may rotate as the telescoping block 1030 moves linearly. In various embodiments, the telescoping block 1030 may be fixedly connected to the distal link 440. The belt 1010 may include grooves on an outer surface of the belt 1010 to mate with teeth provided in links 1020, 1040. The counterweight block 920 may be fixedly coupled to a linear slide provided in the proximal link 430.

FIG. 13B shows an exemplary configuration of the pulley structure according to an embodiment of the present disclosure. In various embodiments, pulleys 1060, 1062 may be coupled to the proximal link 430 via a truss component 1070. For instance, a portion of the truss component 1070 may be fixedly attached to the proximal link 430 and another portion may be attached to axles (not shown) of the pulleys 1060, 1062. The truss component 1070 may also include an extended tubular portion 1072 (which may also be an outer tube), which may house the tubular member 654. The extended tubular portion 1072 may be rigid, and may act as a cantilever for pulleys 1064, 1066. For example, in various embodiments, the extended tubular portion 1072 may be fixedly connected to a suspension portion 1074, which may be attached to the axles (not shown) of the pulleys 1064, 1066. In this way, the suspension portion 1074, and therefore the pulleys 1064, 1066, may be suspended at a distal end of the extended tubular portion 1072, as shown in FIG. 13B. As the distal link 440 extends out from and retracts within the channel 435 of the proximal link 430, the pulleys 1060, 1062, 1064, 1066 remain in the channel 435 of the proximal link 430 due to the above connections associated with the truss component 1070, the suspension portion 1074, and the axles of the pulleys 1060, 1062, 1064, 1066.

As the FIM 417 and the distal link 440 extend out from the proximal link 430, the telescoping block 1030 extends out of the proximal link 430. Because the telescoping block 1030 is fixedly connected to the lower portion 1014 of the belt 1010 at link 1040, and the pulleys 1060, 1062, 1064, 1066 are fixedly connected to the proximal link 430, the belt 1010 rotates in the clockwise direction around the pulleys 1060, 1062, 1064, 1066. As a result, the counterweight block 920 (see FIG. 13A), which is fixedly connected to the upper portion 1012 of the belt 1010 at link 1020, linearly moves towards the pivot point C along with the clockwise rotation of the belt 1010. Thus, equilibrium is maintained at the pivot point C because the mass (or weight) of the counterweight block 920 is substantially equal to the mass (or weight) of the FIM 417 plus the support structure 420, and because the counterweight block 920 is moved by a distance substantially equal to the movement of the FIM 417 (increase in L). This allows nullification of the effects of gravity on the movement of the FIM 417 and the support structure 420.

Similarly, as the distal link 440 retracts within the proximal link 430, the telescoping block 1030 also retracts in the proximal link 430. Because the telescoping block 1030 is fixedly connected to the lower portion 1014 of the belt 1010 at link 1040, and the pulleys 1060, 1062, 1064, 1066 are fixedly connected to the proximal link 430, the belt 1010 rotates in the counter-clockwise direction around the pulleys 1060, 1062, 1064, 1066. As a result, the counterweight block 920 (see FIG. 13A), which is fixedly connected to the upper portion 1012 of the belt 1010 at link 1020, linearly moves towards the distal support 450 along with the counter-clockwise rotation of the belt 1010. Thus, equilibrium is again maintained at the pivot point C because the mass (or weight) of the counterweight block 920 is substantially equal to the mass of the FIM 417 plus the support structure 420, and because the counterweight block 920 is moved by a distance substantially equal to the movement of the FIM 417 (decrease in L). This counterbalancing allows nullification of the effects of gravity on the movement of the FIM 417 and the support structure 420.

FIG. 14 shows another exemplary configuration of the support structure 420 at equilibrium about the pivot point C, according to an embodiment of the present disclosure. In various embodiments, the linear movement of the counterweight block 920 may be enabled by motorized rotation of the belt 1010. The configuration shown in FIG. 14 is similar to the configuration shown in FIG. 13A, but the configuration shown in FIG. 14 includes a motor 1130 (instead of the telescoping block 1030) coupled to the belt 1010 at link 1140 such that the motor 1130 may enable the belt 1010 to rotate in the clockwise or the counter-clockwise directions. The motor 1130 may be powered and controlled by an encoder 1150 electrically connected to the motor 1130 via electrical wires 1160.

As the FIM 417 and the distal link 440 extend out from the proximal link 430, the encoder 1150 senses the extension of the distal link 440 and controls the motor 1130 to allow clockwise rotation of the belt 1010 around the pulleys 1060, 1062, 1064, 1066. As a result, the counterweight block 920, which is fixedly connected to the upper portion 1012 of the belt 1010 at link 1020, linearly moves towards the pivot point C along with the clockwise rotation of the belt 1010. Thus, equilibrium is maintained at the pivot point C because the mass of the counterweight block 920 is substantially equal to the mass of the FIM 417 plus the support structure 420, and because the counterweight block 920 is moved by a distance substantially equal to the movement of the FIM 417 (increase in L). This allows nullification of the effects of gravity on the movement of the FIM 417 and the support structure 420.

Similarly, as the distal link 440 retracts within the proximal link 430, the encoder 1150 senses the retraction of the distal link 440 and controls the motor 1130 to allow counter-clockwise rotation of the belt 1010 around the pulleys 1060, 1062, 1064, 1066. As a result, the counterweight block 920, which is fixedly connected to the upper portion 1012 of the belt 1010 at link 1020, linearly moves towards the distal support 450 along with the counter-clockwise rotation of the belt 1010. Thus, equilibrium is again maintained at the pivot point C because the mass of the counterweight block 920 is substantially equal to the mass of the FIM 417 plus the support structure 420, and because the counterweight block 920 is moved by a distance substantially equal to the movement of the FIM 417 (decrease in L). Again, this allows nullification of the effects of gravity on the movement of the FIM 417 and the support structure 420.

FIG. 18 is a flowchart illustrating a general method 1700 for use in an image guided surgical procedure. At a process 1702, pre-operative or intra-operative image data is obtained from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may correspond to two-dimensional, three-dimensional, or four-dimensional (including e.g., time based or velocity based information) images. For example, the image data may represent the human lungs 201 of FIG. 7.

At a process 1704, computer software alone or in combination with manual input is used to convert the recorded images into a segmented two dimensional or three dimensional composite representation or model of a partial or an entire anatomical organ or anatomical region. The composite representation and the image data set describe the various locations and shapes of the passageways and their connectivity. More specifically, during the segmentation process the images are partitioned into segments or elements (e.g., pixels or voxels) that share certain characteristics or computed properties such as color, density, intensity, and texture. This segmentation process results in a two- or three-dimensional reconstruction that forms a model of the target anatomy based on the obtained image. To represent the model, the segmentation process may delineate sets of voxels representing the target anatomy and then apply a function, such as marching cube function, to obtain a 3D surface that encloses the voxels. This segmentation process results in a two- or three-dimensional reconstruction that forms a model of the target anatomy based on the obtained image. To represent the model, the segmentation process may delineate sets of voxels representing the target anatomy and then apply a function, such as marching cube function, to obtain a 3D surface that encloses the voxels. Additionally or alternatively, the model may include a centerline model that includes a set of interconnected line segments or points extending through the centers of the modeled passageways. Where the model includes a centerline model including a set of interconnected line segments, those line segments may be converted to a cloud or set of points. By converting the line segments, a desired quantity of points corresponding to the interconnected line segments can be selected manually or automatically.

At a process 1706, the anatomic model data is registered to the patient anatomy prior to and/or during the course of an image-guided surgical procedure on the patient. Generally, registration involves the matching of measured point to points of the model through the use of rigid and/or non-rigid transforms. Measured points may be generated using landmarks in the anatomy, electromagnetic coils scanned and tracked during the procedure, or a shape sensor system. The measured points may be generated for use in an iterative closest point (ICP) technique described elsewhere in this disclosure. Other point set registration methods may also be used in registration processes within the scope of this disclosure.

Registration methods for use with image-guided surgery often involve the use of technologies based on electromagnetic or impedance sensing. Metallic objects or certain electronic devices used in the surgical environment may create disturbances that impair the quality of the sensed data. Other methods of registration may obstruct the clinical workflow. The systems and methods described below perform registration based upon ICP, or another point set registration algorithm, and the calibrated movement of a point gathering instrument with a fiber optic shape sensor, thus eliminating or minimizing disruptions in the surgical environment. Other registration techniques may be used to register a set of measured points to a pre-operative model or a model obtained using another modality. In the embodiments described below, EM sensors on the patient and the instrument and optical tracking systems for the instrument may be eliminated.

Various systems for using sensors to register and display a medical implement together with preoperatively recorded surgical images, such as those from a virtual visualization system, are known. For example U.S. patent application Ser. No. 13/107,562 (filed May 13, 2011)(disclosing "Medical System Providing Dynamic Registration of a Model of an Anatomical Structure for Image-Guided Surgery"), which is incorporated by reference herein in its entirety, discloses such systems.

Any reference to surgical instruments and surgical methods is non-limiting as the instruments and methods described herein may be used for animals, human cadavers, animal cadavers, portions of human or animal anatomy, non-surgical diagnosis, industrial systems, and general tele-operational or teleoperational systems.

Although the systems and methods of this disclosure have been described for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like. Also, although the systems and methods of this disclosure have been described in connection with detecting the precise location of a mass/tumor for the purposes of conducting a biopsy, the presently disclosed systems and methods may also be used for purposes of delivering treatment. For example, the present systems and methods may be used for delivering pharmaceutical medication or for delivering radiation treatment to precise locations in anatomical passageways within a patient's body. In various embodiments, the delivery of pharmaceutical medication or radiation treatment may be tele-operatively or automatically performed under the control of the teleoperated medical system 100 of FIG. 1.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

The processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical system comprising:
   a support structure including a proximal link and a distal link;
   a base joint coupling the proximal link of the support structure to a base, wherein the proximal link is configured to rotate about a first axis associated with the base joint;
   a linkage mechanism coupling the proximal link to the distal link; and
   an instrument support coupled to the distal link, wherein the instrument support has an orientation relative to the base in a first configuration of the support structure,
   wherein the linkage mechanism maintains the orientation of the instrument support relative to the base as the support structure is moved into a second configuration in which the support structure is rotated relative to the base about the first axis and the distal link is extended from the proximal link.

2. The medical system of claim 1, wherein the distal link is sized to extend within a channel of the proximal link and wherein a length of the support structure is variable with movement of the distal link within the channel.

3. The medical system of claim 1, wherein the proximal link is configured to rotate about a second axis associated with the base joint and wherein the linkage mechanism maintains the orientation of the instrument support relative to the base as the support structure is moved into a third configuration in which the support structure is rotated relative to the base about the first and second axes.

4. The medical system of claim 1, wherein the instrument support is coupled to an instrument manipulator and wherein the linkage mechanism maintains a relative orientation of the instrument manipulator to the base as the support structure is moved into the second configuration in which the support structure is rotated relative to the base about the first axis.

5. The medical system of claim 1, wherein the instrument support is coupled to a medical instrument and wherein the linkage mechanism maintains a relative orientation of the medical instrument to the base as the support structure is moved into the second configuration in which the support structure is rotated relative to the base about the first axis.

6. The medical system of claim 1, further comprising:
a counterbalance mechanism comprising a counterweight block configured to move linearly within the support structure, the counterweight block having a counterweight mass to counterbalance linear movement of the support structure as the distal link extends from the proximal link.

7. The medical system of claim 6, wherein the counterbalance mechanism further comprises a spring coupled to the base joint.

8. The medical system of claim 6, wherein the counterweight block is configured to move by a distance substantially equal to a distance by which the distal link extends from the proximal link.

9. The medical system of claim 1, wherein the linkage mechanism comprises:
an input gear coupled to the base joint;
an output gear coupled to the instrument support;
an input pinion engaged with the input gear;
an output pinion engaged with the output gear; and
an extension mechanism coupled between the input and output pinions.

10. The medical system of claim 9, wherein the extension mechanism comprises:
a spline coupled to the output pinion; and
a tubular member coupled to the input pinion,
wherein the spline is slidable within the tubular member.

11. The medical system of claim 10, wherein the spline is coupled to rotate with the tubular member about a linear axis through the extension mechanism.

12. The medical system of claim 9, wherein the input gear and the output gear are disposed on opposite sides of a linear axis through the extension mechanism.

13. The medical system of claim 9, wherein the first axis is through the input gear and the input gear is rotationally stationary with respect to the base, and wherein the output gear is configured to rotate about the first axis.

14. The medical system of claim 13, wherein the output gear is configured to rotate about the first axis while maintaining an orientation of the output gear relative to the input gear.

15. The medical system of claim 1, wherein the linkage mechanism comprises:

a first push-pull cylinder; and
a second push-pull cylinder,
wherein the base joint includes an input disk connected to a piston of the first push-pull cylinder and to a cylinder of the second push-pull cylinder via respective hinged connections.

16. The medical system of claim 15, wherein the instrument support is connected to an output disk connected to a cylinder of the first push-pull cylinder and to a piston of the second push-pull cylinder via respective hinged connections.

17. The medical system of claim 1, wherein the linkage mechanism comprises first and second ball screw drives, and
wherein the base joint comprises an input disk connected to an extended ball nut of the first ball-screw drive and to a ball screw of the second ball-screw drive via respective hinged joints.

18. The medical system of claim 17, wherein the instrument support is connected to an output gear that is connected to a ball screw of the first ball-screw drive and to an extended ball nut of the second ball-screw drive via respective hinged joints.

19. The medical system of claim 18, wherein the first ball-screw drive and the second ball-screw drive are connected by a flexible shaft to enable the first and second ball-screw drives to rotate at a same rate with respect to each other.

20. The medical system of claim 18, wherein the first ball-screw drive is configured to rotate in a direction opposite to a direction of rotation of the second ball-screw drive.

21. The medical system of claim 1, wherein the linkage mechanism comprises:
an input pulley;
an output pulley;
at least one inner pulley; and
a chain,
wherein the chain is coupled to an outer edge of the input pulley, an outer edge of the output pulley, and an outer edge of the at least one inner pulley.

22. The medical system of claim 21, wherein the instrument support is coupled to the output pulley, and wherein the chain enables the input pulley and the output pulley to rotate an equivalent degree of rotation.

23. The medical system of claim 21, wherein the at least one inner pulley is coupled to a counterbalance mechanism comprising a counterweight block, and
wherein the counterweight block is configured to move by a distance substantially equal to a distance by which the distal link extends from the proximal link.

24. The medical system of claim 21, wherein the linkage mechanism further comprises a second inner pulley,
wherein the at least one inner pulley and the second inner pulley are coupled to a counterbalance mechanism comprising a counterweight block, and
wherein the counterweight block is configured to move by a distance substantially equal to a distance by which the distal link extends from the proximal link.

* * * * *